United States Patent
Rajalingam et al.

(10) Patent No.: US 8,658,615 B2
(45) Date of Patent: Feb. 25, 2014

(54) PROHIBITIN AS TARGET FOR CANCER THERAPY

(75) Inventors: Krishnaraj Rajalingam, Berlin (DE); Thomas Rudel, Berlin (DE)

(73) Assignee: AEterna Zentaris GmbH, Frankfurt (DE)

( * ) Notice: Subject to any disclaimer, the term of this patent is extended or adjusted under 35 U.S.C. 154(b) by 92 days.

(21) Appl. No.: 13/275,666

(22) Filed: Oct. 18, 2011

(65) Prior Publication Data

US 2012/0121575 A1    May 17, 2012

Related U.S. Application Data

(63) Continuation of application No. 11/663,591, filed as application No. PCT/EP2005/010339 on Sep. 23, 2005, now abandoned.

(30) Foreign Application Priority Data

Sep. 23, 2004   (EP) ..................................... 04022730

(51) Int. Cl.
   *C12N 15/113*   (2010.01)
   *C07H 21/04*    (2006.01)

(52) U.S. Cl.
   USPC ........................ 514/44 A; 536/24.5

(58) Field of Classification Search
   None
   See application file for complete search history.

(56) References Cited

U.S. PATENT DOCUMENTS

| | | | |
|---|---|---|---|
| 5,463,026 A | 10/1995 | Nakamura et al. | |
| 5,658,792 A | 8/1997 | Nuell et al. | |
| 7,273,855 B2 * | 9/2007 | Jupe ............................ | 514/44 R |

FOREIGN PATENT DOCUMENTS

| | | |
|---|---|---|
| WO | 00/05359 | 2/2000 |
| WO | 00/05359 A | 2/2000 |

OTHER PUBLICATIONS

Mishra et al. Trends in Molecular Medicine 2005, vol. 11, pp. 192-197.*
Bocchetta et al. Oncogene 2004, vol. 23, pp. 6484-6491.*
Gamble et al., "Androgens target prohibitin to regulate proliferation of prostate cancer cells," Oncogene, vol. 23, No. 17, Apr. 15, 2004, pp. 2996-3004.
Rajalingam et al., "Prohibitin is required for Ras-induced Raf-MEK-ERK activation and epithelial cell migration," Nature Cell Biology, Aug. 2005, vol. 7, No. 8, Aug. 2005, pp. 837-843.
Synder et al., "A novel role for prohibitin in melanogenesis discovered using small-molecule probes," Journal of Investigative Dermatology, vol. 122, No. 3, Mar. 2004, p. A155.
Wang et al., "BRG1/BRM and prohibitin are required for growth suppression by estrogen antagonists," EMBO, vol. 23, No. 11, Jun. 2, 2004, pp. 2293-2303.
Downward, Julian, "Targeting RAS signalling pathways in cancer therapy", Nature Reviews Cancer, vol. 3, No. 1, Jan. 2003, pp. 11-22, ISSN: 1474-175X.
Kolch, Walter et al., "The role of Raf kinases in malignant transformation", Apr. 25, 2002, ISSN: 1462-3994, Retrieved from the Internet: URL:www. Expertreviews.org.
Mullen, Peter et al., "Antisense oligonucleotide targeting of Raf-1: importance of raf-1 mRNA expression levels and raf-1-dependent signaling in determining growth response in ovarian cancer", Clinical Cancer Research: an Official Journal of the American Association for Cancer Research, Mar. 15, 2004, LNKD-PUBMED: 15041731, vol. 10, No. 6, pp. 2100-2108, ISSN: 1078-0432.
Wang, Sheng et al. "RB and prohibitin target distinct regions of E2F1 for repression and respond to different upstream signals", Molecular and Cellular Biology, American Society for Microbiology, Washington, US, vol. 19, No. 11, Nov. 1, 1999, pp. 7447-7460, XP008074841, ISSN: 0270-7306.
Summons to attend oral proceedings pursuant to Rule 115(1) EPC in application No. 05792945.7-2406/1791957 dated Jan. 7, 2011 (10 pages).
Kolonin, M.G. et al., "Reversal of obesity by targeted ablation of adipose tissue," Nature Medicine, vol. 10, No. 6, May 9, 2004, pp. 625-632.
Mishra, Suresh et al., "The Prohibitins: emerging roles in diverse functions," Journal of Cellular and Molecular Medicine, vol. 10, No. 2, Apr. 1, 2006-Jun. 30, 2006, pp. 353-363.
Snyder, J. R. et al., "Dissection of melanogenesis with small molecules identifies prohibitin as a regulator," Chemistry & Biology, vol. 12, Apr. 1, 2005, pp. 477-484.
Czarnecka et al., "Mitochondrial Chaperones in Cancer," Cancer Biology & Therapy, 2006; vol. 5, Issue 7, pp. 714-720.
Jupe, et al., "Prohibitin in Breast Cancer Cell Lines: Loss of Antiproliferative Activity is Linked to 3' Untranslated Region Mutations", Cell Growth & Differentiation, vol. 7, Jul. 1996, pp. 871-878.
Manjeshwar et al., "Tumor Suppression by the Prohibitin Gene 3'Ultranslated Region RNA in Human Breast Cancer", Cancer Research 63, Sep. 1, 2003, pp. 5251-5256.
Embo J., vol. 23, Jun. 2004, p. 2293-2303.

* cited by examiner

*Primary Examiner* — Tracy Vivlemore
(74) *Attorney, Agent, or Firm* — Rothwell, Figg, Ernst & Manbeck, P.C.

(57) ABSTRACT

The present invention relates to pharmaceutical compositions comprising inhibitors of Prohibitin (PHB) for the prevention or/and treatment of hyperproliferative disorders.

25 Claims, 10 Drawing Sheets

Figure 1:
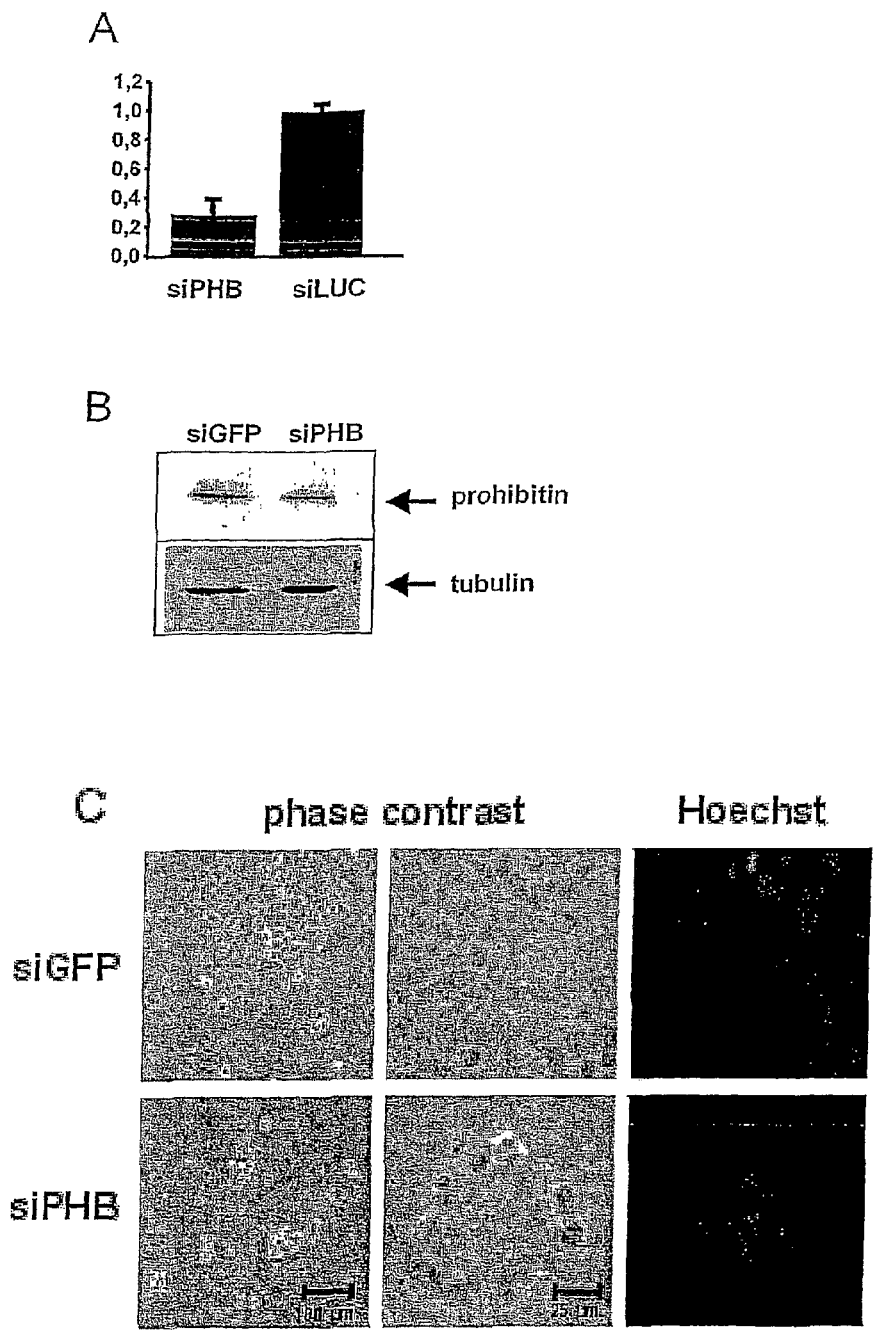
Figure 1:
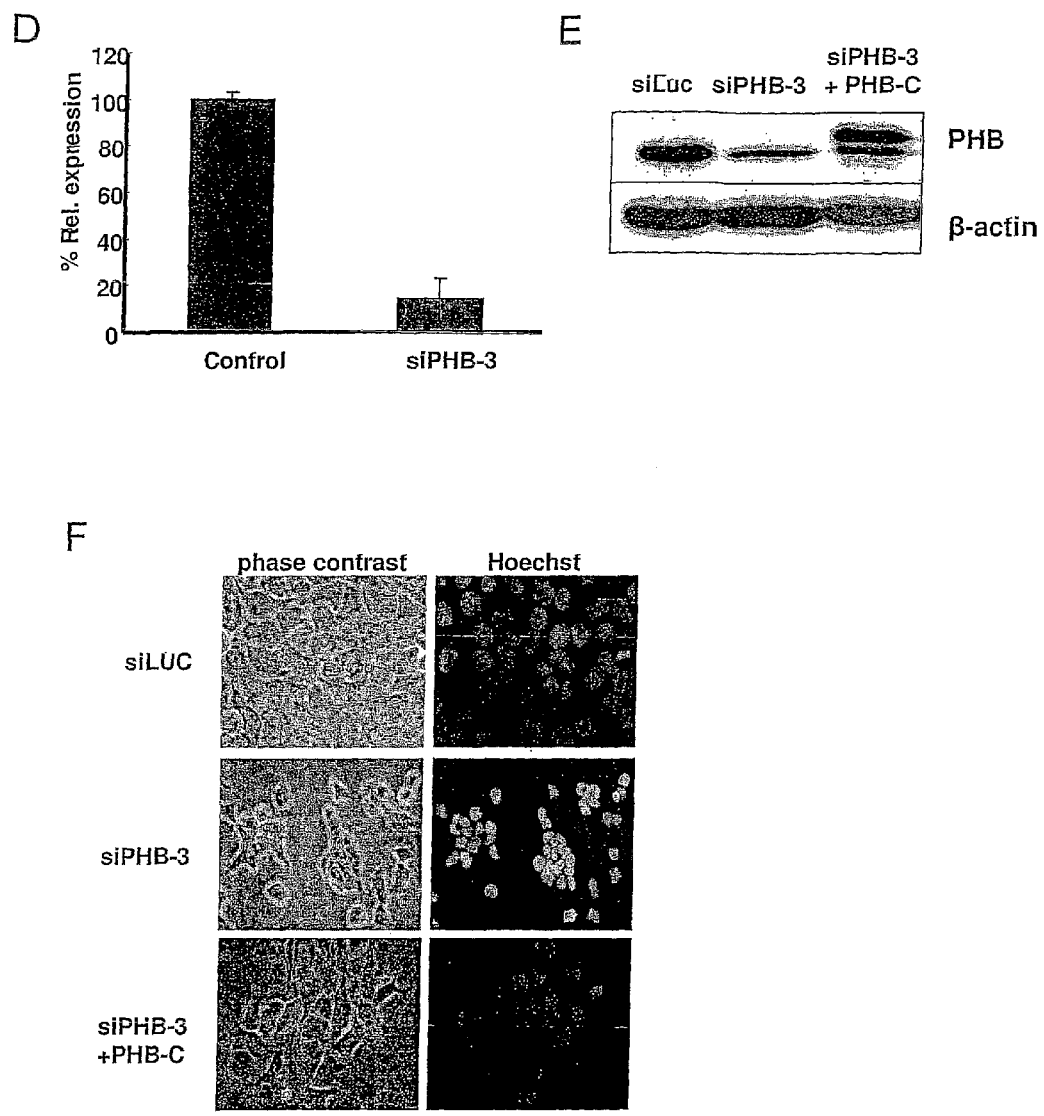

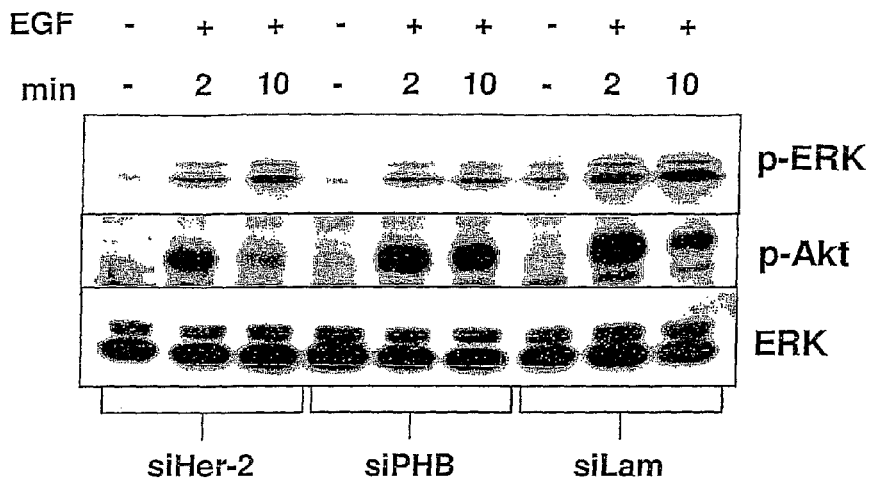
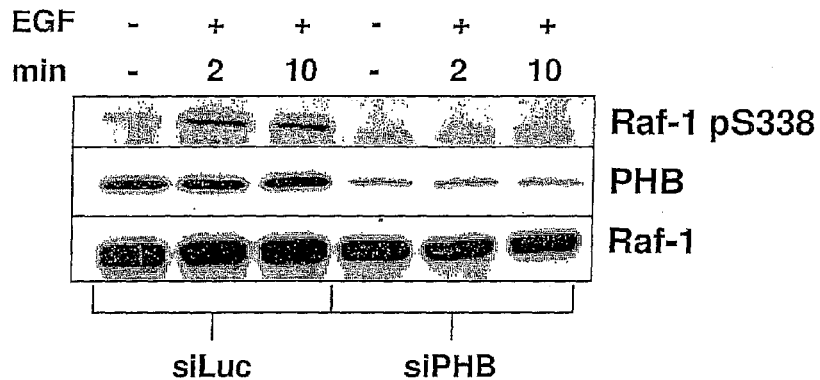
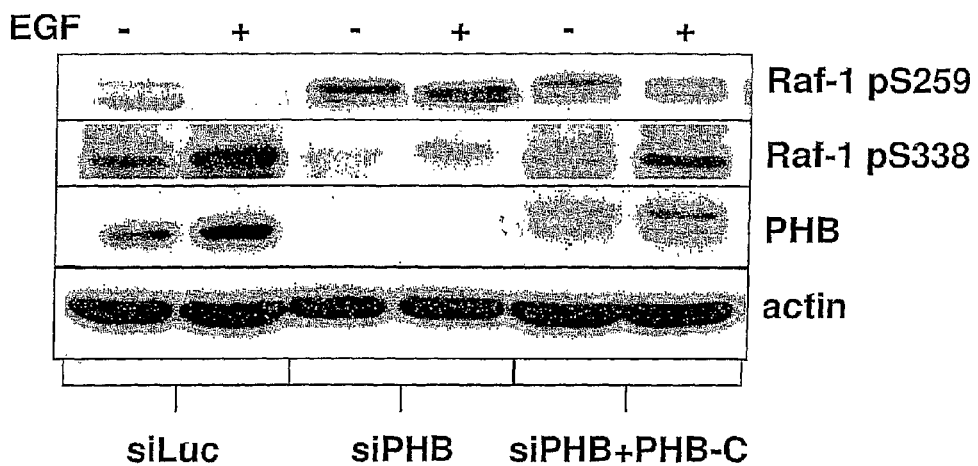
Figure 3

E
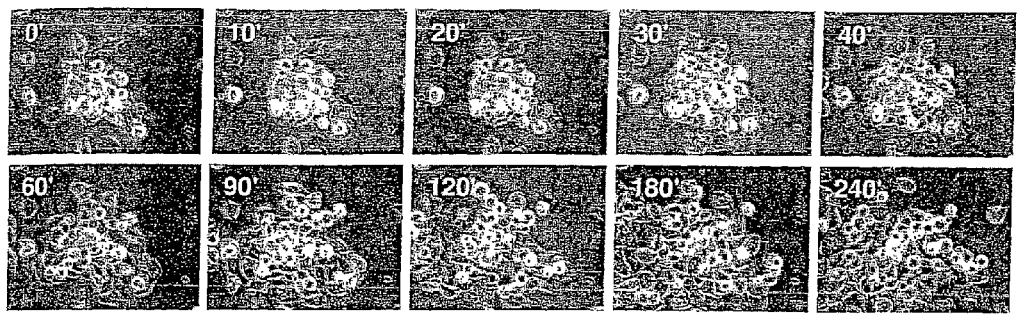
F
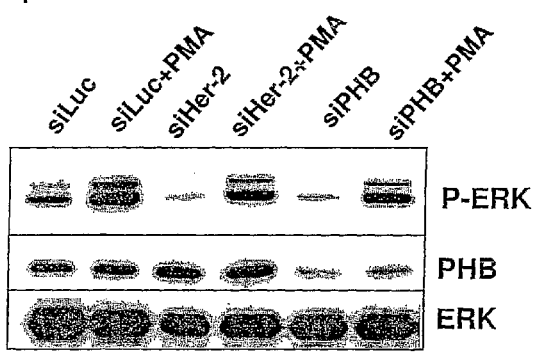
H
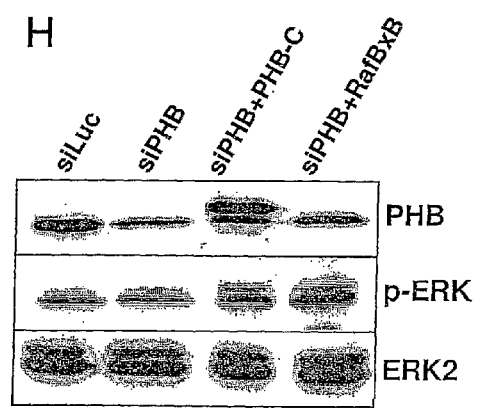
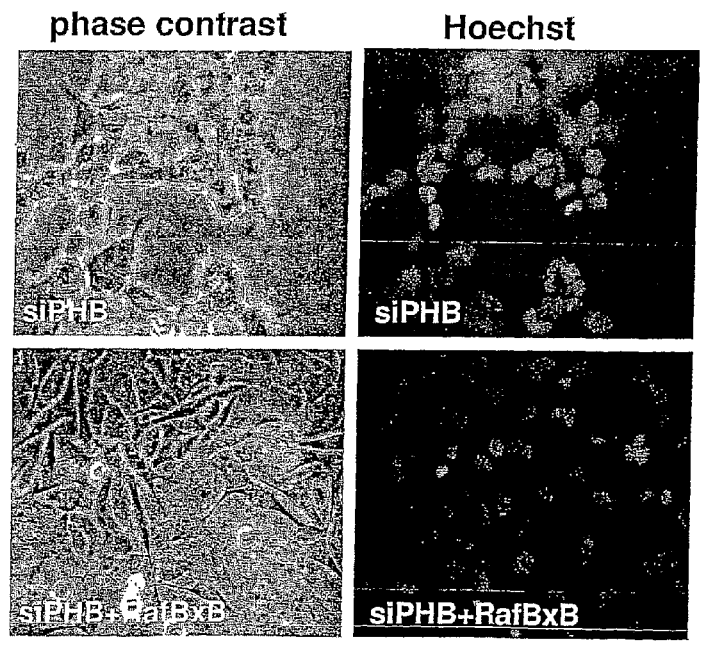
Figure 3
Continued

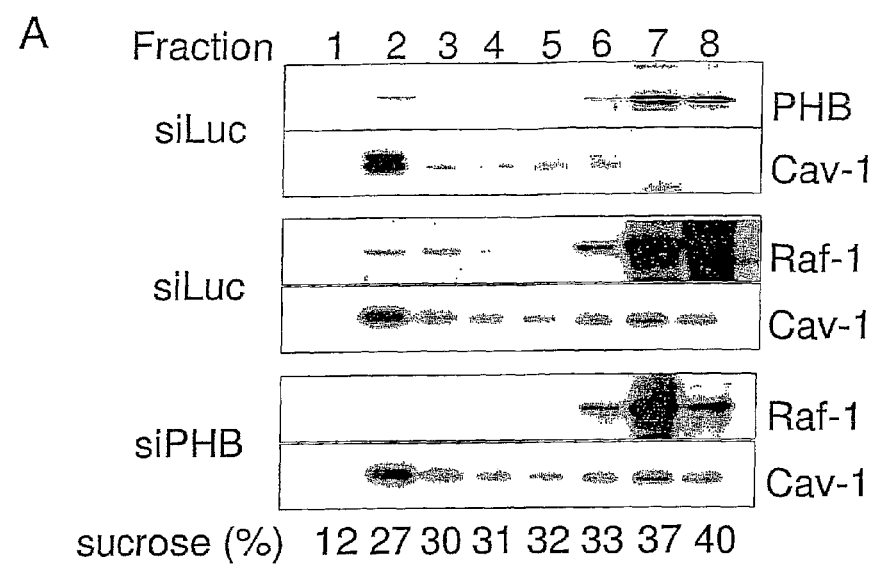
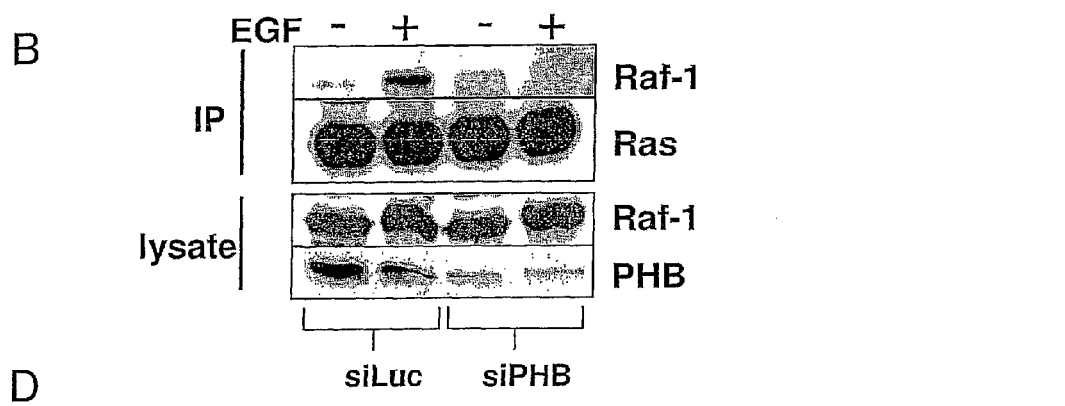
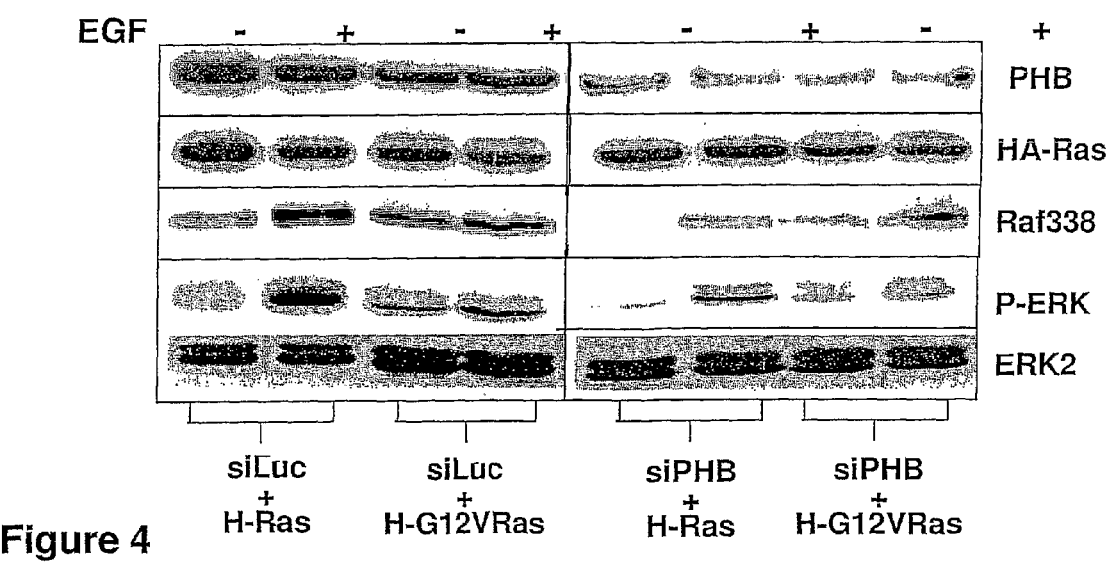
Figure 4

Figure 5

Prohibitin mRNA (NM_002634)

```
AGTATGTGTGGTTGGGGAATTCATGTGGAGGTCAGAGTGGAAGCAGGTGTGAGAGGGTCC
AGCAGAAGGAAACATGGCTGCCAAAGTGTTTGAGTCCATTGGCAAGTTTGGCCTGGCCTT
AGCTGTTGCAGGAGGCGTGGTGAACTCTGCCTTATATAATGTGGATGCTGGGCACAGAGC
TGTCATCTTTGACCGATTCCGTGGAGTGCAGGACATTGTGGTAGGGGAAGGGACTCATTT
TCTCATCCCGTGGGTACAGAAACCAATTATCTTTGACTGCCGTTCTCGACCACGTAATGT
GCCAGTCATCACTGGTAGCAAAGATTTACAGAATGTCAACATCACACTGCGCATCCTCTT
CCGGCCTGTCGCCAGCCAGCTTCCTCGCATCTTCACCAGCATCGGAGAGGACTATGATGA
GCGTGTGCTGCCGTCCATCACAACTGAGATCCTCAAGTCAGTGGTGGCTCGCTTTGATGC
TGGAGAACTAATCACCCAGAGAGAGCTGGTCTCCAGGCAGGTGAGCGACGACCTTACAGA
GCGAGCCGCCACCTTTGGGCTCATCCTGGATGACGTGTCCTTGACACATCTGACCTTCGG
GAAGGAGTTCACAGAAGCGGTGGAAGCCAAACAGGTGGCTCAGCAGGAAGCAGAGAGGGC
CAGATTTGTGGTGGAAAAGGCTGAGCAACAGAAAAAGGCGGCCATCATCTCTGCTGAGGG
CGACTCCAAGGCAGCTGAGCTGATTGCCAACTCACTGGCCACTGCAGGGGATGGCCTGAT
CGAGCTGCGCAAGCTGGAAGCTGCAGAGGACATCGCGTACCAGCTCTCACGCTCTCGGAA
CATCACCTACCTGCCAGCGGGGCAGTCCGTGCTCCTCCAGCTGCCCCAGTGAGGGCCCAC
CCTGCCTGCACCTCCGCGGGCTGACTGGGCCACAGCCCCGATGATTCTTAACACAGCCTT
CCTTCTGCTCCCACCCCAGAAATCACTGTGAAATTTCATGATTGGCTTAAAGTGAAGGAA
ATAAAGGTAAAATCACTTCAGATCTCTAATTAGTCTATCAAATGAAACTCTTTCATTCTT
CTCACATCCATCTACTTTTTTATCCACCTCCCTACCAAAAATTGCCAAGTGCCTATGCAA
ACCAGCTTTAGGTCCCAATTCGGGGCCTGCTGGAGTTCCGGCCTGGGCACCAGCATTTGG
CAGCACGCAGGCGGGGCAGTATGTGATGGACTGGGGAGCACAGGTGTCTGCCTAGATCCA
CGTGTGGCCTCCGTCCTGTCACTGATGGAAGGTTTGCGGATGAGGGCATGTGCGGCTGAA
CTGAGAAGGCAGGCCTCCGTCTTCCCAGCGGTTCCTGTGCAGATGCTGCTGAAGAGAGGT
GCCGGGGAGGGGCAGAGAGGAAGTGGTCTGTCTGTTACCATAAGTCTGATTCTCTTTAAC
TGTGTGACCAGCGGAAACAGGTGTGTGTGAACTGGGCACAGATTGAAGAATCTGCCCCTG
TTGAGGTGGGTGGGCCTGACTGTTGCCCCCCAGGGTCCTAAAACTTGGATGGACTTGTAT
AGTGAGAGAGGAGGCCTGGACCGAGATGTGAGTCCTGTTGAAGACTTCCTCTCTACCCCC
CACCTTGGTCCCTCTCAGATACCCAGTGGAATTCCAACTTGAAGGATTGCATCCTGCTGG
GGCTGAACATGCCTGCCAAAGACGTGTCCGACCTACGTTCCTGGCCCCCTCGTTCAGAGA
CTGCCCTTCTCACGGGCTCTATGCCTGCACTGGGAAGGAAACAAATGTGTATAAACTGCT
GTCAATAAATGACACCCAGACCTTCC
```

Figure 6

Prohibitin amino acid sequence

```
MAAKVFESIGKFGLALAVAGGVVNSALYNVDAGHRAVIFDRFRGVQDIVVGEGTHFLIPW
VQKPIIFDCRSRPRNVPVITGSKDLQNVNITLRILFRPVASQLPRIFTSIGEDYDERVLP
SITTEILKSVVARFDAGELITQRELVSRQVSDDLTERAATFGLILDDVSLTHLTFGKEFT
EAVEAKQVAQQEAERARFVVEKAEQQKKAAIISAEGDSKAAELIANSLATAGDGLIELRK
LEAAEDIAYQLSRSRNITYLPAGQSVLLQLPQ
```

PROHIBITIN AS TARGET FOR CANCER THERAPY

This application is continuation of U.S. Ser. No. 11/663,591 filed Apr. 30, 2007, which is a 35 U.S.C. 371 National Phase Entry Application from PCT/EP2005/010339, filed Sep. 23, 2005, which claims the benefit of European Patent Application No. EP 04 022 730.8 filed on Sep. 23, 2004, the disclosures of which are incorporated herein in its entirety by reference.

The present invention relates to pharmaceutical compositions comprising inhibitors of Prohibitin (PHB) for the prevention or/and treatment of hyperproliferative disorders. Further, the present invention concerns PHB inhibitors and screening methods for identification of PHB inhibitors, which inhibitors are suitable for prevention or/and treatment of hyperproliferative disorders.

Ras-MAPK cascade has been activated in almost all tumours and plays a very important role in proliferation, tumour cell migration, invasion of the extracellular matrix, resistance to apoptosis and angiogenesis (ability to induce new blood vessel formation). There are at least 20 new therapeutic agents in clinical trials at present exploiting the interaction and activation of several components of this highly conserved pathway. This includes a range of Farnesyl transferase inhibitors (FTIs) to block the translocation of Ras to the plasma membrane, for example the drug R115777 (Zanestra is in clinical trail phase III), SCH66336 (SARASAR), to antisense oligonucleotides to Raf and H-Ras (ISIS5132 and ISIS25403) from Isis pharmaceuticals. Apart from targeting the Ras-MAPK cascade there are also several drugs targeting upstream pathways most importantly the EGF receptor family members. As EGFR or its family members is found to be highly expressed in more than 50% of carcinomas. Most importantly Her-2, an EGFR family member is amplified and therefore the causative for breast cancer. The drugs which target these members range from kinase inhibitors like the OSI-774 (Tarceva) to the well known Herceptin (Transtuzumab, a humanized antibody) which is now licensed for use on breast cancer. The major aim of these drugs is to reduce the hyper activation of Ras-MAPk kinase cascade and sensitize them to chemotherapeutic cancer drugs. As we have identified PHB as a new modulator of this known pathway, targeting PHB could be a potential alternative in all these cases.

Ras proteins control signalling pathways responsible for normal growth and malignant transformation. Raf protein kinases are direct Ras effector proteins initiating the mitogen-activated protein (MAP) kinase cascade leading to the activation of transcription factors via ERK. Here we show, that prohibitin (PHB), a ubiquitously expressed and evolutionarily conserved protein is indispensable for the activation of the Raf-MAP kinase pathway by Ras. Raf kinase fails to interact with active Ras induced by epidermal growth factor (EGF) in the absence of prohibitin. Prohibitin and Raf kinase are enriched in caveolae and after depletion of prohibitin, Raf kinase is lost from this compartment. Constitutively active Raf kinase induces ERK activation independent of prohibitin. Interestingly, we find a prominent role of the prohibitin dependent branch of the Ras signalling pathway in epithelial cell adhesion and migration. In prohibitin deficient cells the adherent complex proteins cadherin and β-catenin relocalise to plasma membrane and thereby stabilize adherent junctions. Our data show an unexpected role of prohibitin in the activation of the Ras-Raf signalling pathway and in modulating epithelial cell adhesion and migration.

Prohibitin (PHB) is involved in diverse cellular processes like proliferation and energy metabolism and is found in different cellular compartments including the nucleus and mitochondria (1). We identified PHB in a RNA interference based loss of function screen for proteins involved in the regulation of apoptosis (Machuy et al., in press). Besides the slight sensitisation for apoptotic stimuli observed (not shown), the most prominent phenotype of HeLa cells transfected with siRNAs to suppress PHB expression (siPHB) was reduced spreading and increased intercellular adhesion to form tiny islands of densely packed cells in place of a uniform monolayer (FIG. 1). The observed phenotype correlated with prohibitin expression because, due to the transient effect of siRNAs, PHB expression was normal 6 days post transfection and the growth of epithelial cell as monolayer was restored (data not shown). In order to exclude unspecific effects of the siRNA used, an additional siRNA designed to target the coding region (siPHB-2) and one to target the 3' untranslated region (siPHB-3) of the prohibitin mRNA were used. All siRNA, siPHB (FIG. 1A,B), siPHB-2 (FIG. S1) and siPHB-3 (FIG. 1E,F) efficiently interfered with the expression of prohibitin and induced a similar phenotype as siPHB (FIG. S1C, FIG. 1C,D). PHB expression was then complemented in siPHB-3 transfected cells by co-transfecting an expression plasmid harbouring the cloned PHB gene. Complemented cells formed monolayers suggesting that the formation of small islands depended on the lack of PHB (FIG. 1D). An similar phenotype could also be detected in other cell types like human larynx carcinoma (HEp-2) and gastric cancer cells (AGS) (not shown).

Figure 2:
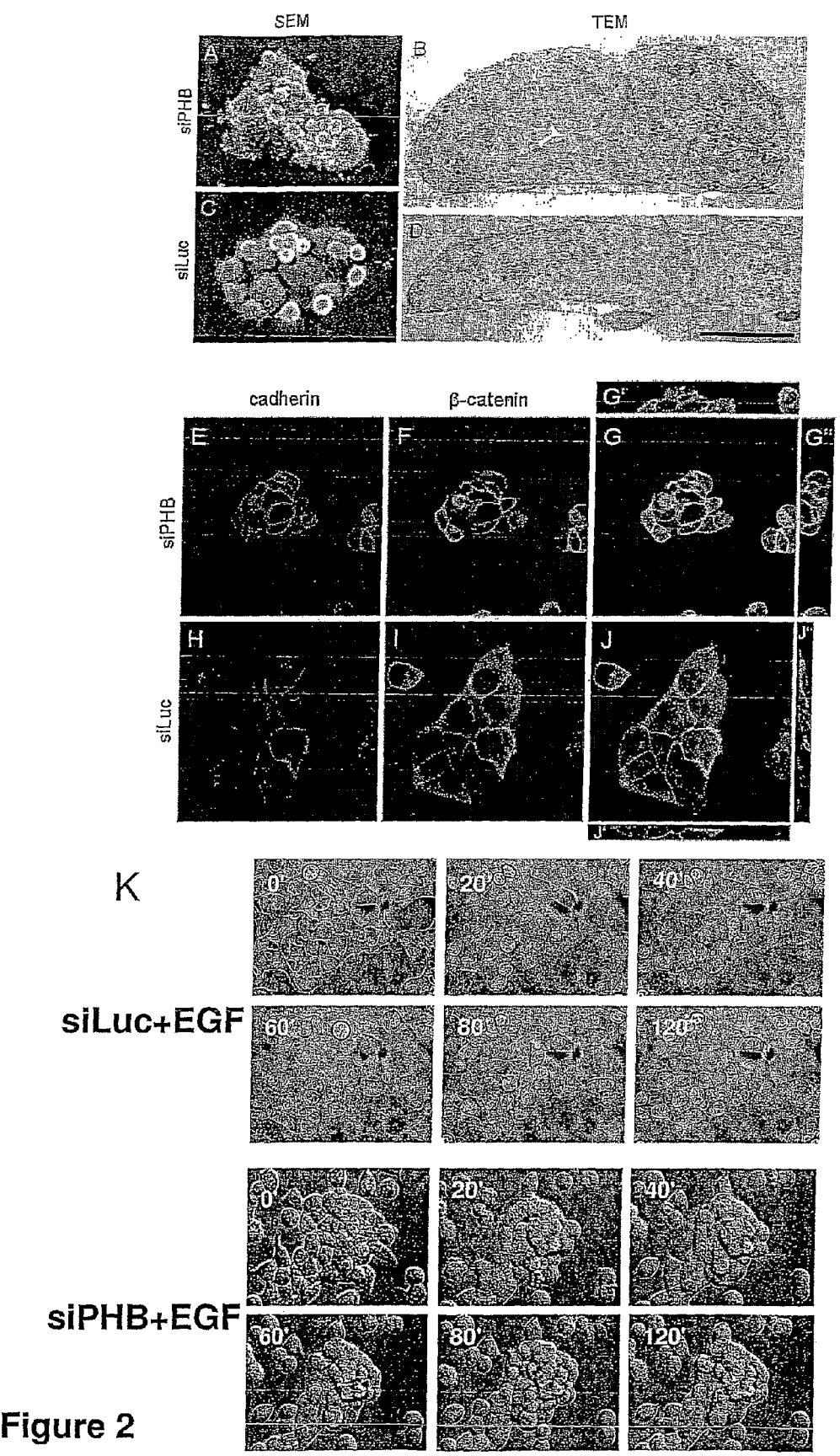

To investigate the nature of intercellular adhesion we performed scanning and transmission electron microscopy studies on cells with silenced PHB expression. FIG. 2 (A-D) shows the SEM and TEM images of the control transfected and siPHB transfected cells. As observed previously, cells transfected with siPHB have almost no intercellular spaces and packed compactly when compared to the control transfected cells. To check if the increased intercellular adhesion was due to the formation and/or stabilization of adherens junctions (AJs), we performed confocal microscopy analysis in the PHB knock down cells. The formation and/or stabilization of the AJs can be studied by monitoring the intracellular localizations of AJ complex proteins like cadherins or β-catenin. In contrast to control cells, PHB knock down cells exhibited a strong staining for both cadherins and β-catenin at the plasma membrane indicating a predominant lateral localization of these junctional proteins resulting in stabilized adherens junctions (FIG. 2) (E-J).

The control of adherens junction formation is an important step of malignant transformation in epithelial cells and has previously been shown to be controlled by receptor tyrosine kinases like the epithelial growth factor receptor (EGFR) and the human EGFR-related 2 (Her-2). Both receptors are deregulated in several epithelial tumours leading to constitutive kinase activity (2) and malignant transformation (3). Stimulation of these receptors with epidermal growth factor (EGF) results in the enhanced migration on collagen (4) or extracellular matrix a widely used in vitro model for studying cancer metastasis (5). HeLa cells lacking PHB expression were defective in such a migration assay (FIG. 2K) suggesting that PHB is required for EGF-induced migration.

We tested then whether down regulation of the Her-2 or EGFR resulted in the formation of cell clusters as previously observed for cells lacking PHB expression. Cells depleted of Her-2 (FIG. S2) or EGFR (not shown) formed cell clusters similar to those observed in cells with reduced PHB expression. Transfection of siPHB had no effect on the amount of surface exposed EGFR (not shown) or Her-2 (FIG. S2), suggesting that PHB is involved in a signalling pathway downstream of EGFR and Her-2.

EGFR and Her-2 signal via Ras proteins to different pathways involved in cell proliferation, migration, differentiation including the Raf-MAPK-ERK or the phosphoinositide 3-kinase (PI3K)-AKT pathway (2,6). Interestingly, depletion of Her-2 or PHB strongly reduced the phosphorylation of ERK but not of AKT suggesting a specific involvement of PHB in the Ras-Raf-MAPK pathway (FIG. 3A). Neither the protein levels of Ras, Raf-1, ERK2 (FIGS. 3 and 4) or MEK-1 (not shown) were reduced in PHB depleted cells ruling out an unspecific inhibitory effect of the transfected siRNA. Furthermore, expression of the cloned PHB gene in siPHB transfected cells restored the EGF-dependent phosphorylation of ERK showing a specific function of PHB in signalling from RTK receptors to ERK (FIG. 3H).

Raf-1 kinase is regulated by phosphorylation at several amino acids. Ser259 is the major target for inhibitory phosphorylation and dephosphorylation of Ser259 generally precedes the activating phosphorylation at the Ser338 (7). As expected, stimulation of HeLa cells with EGF caused an increased phosphorylation of Raf-1 at Ser338 (FIG. 3D). Interestingly, cells lacking PHB lacked the basal as well as the EGF induced phosphorylation at Ser338 indicative of a block in Raf-1 kinase activation by PHB depletion (FIG. 3D). Moreover, in the absence of PHB, no alteration or relatively high levels of Raf-1 phosphorylated at Ser259 were detected (FIG. 3D). Restoration of PHB expression by complementing the siPHB transfected cells with the cloned PHB gene restored the basal as well as EGF-dependent activation of Raf-1, apparent by high Raf-1 pSer338 and low Raf-1 pSer259 levels (FIG. 3D). Thus, PHB is required for EGF-induced Raf-1 activation.

If PHB is involved in the activation of Raf-1-MEK-ERK, cell clusters induced by reduced motility and stabilized adherens junctions should be affected by direct activation of Raf-1 or the expression of a constitutively active Raf-1 derivative. Treatment of siPHB transfected cells with phorbol myristate acetate (PMA), an activator of Raf-1 (8), rapidly resolved the cell clusters formed upon PHB depletion in between 2 to 4 hours upon addition (FIG. 3E; see also supplementary movie). As expected, PMA treated cells showed increased ERK phosphorylation irrespective of the presence or absence of PHB (FIG. 3F). Likewise, expression of a constitutive active Raf-1 mutant RafBXB (9) was sufficient to prevent clusters formation in cells with silenced PHB expression (FIG. 3G,H). RafBXB expression stimulated the phosphorylation of ERK in siPHB-3 transfected cells to a similar extent as the transgenic expression of the cloned PHB gene (FIG. 3G,H). Taken together, these data demonstrate a direct role of PHB in the activation of Raf-1.

Activation of Raf-1 requires the Ras-dependent recruitment to the plasma membrane (10,11) where both proteins reside in special caveolin rich patches called caveolae (12). PHB has previously been shown to localise to the plasma membrane and further a direct interaction of PHB and Raf-1 was also reported in U937 cells (13). We have also detected Raf-1, as well as Raf-1 pS338 in the PHB immunoprecipitates from Hela cells treated with or without EGF (FIG. S3). Interestingly, we also found PHB in caveolae together with Raf-1 (FIG. 4A). However, Raf-1 was not detected in the caveolae of siPHB treated cells (FIG. 4A), suggesting that PHB is required at a step prior to membrane recruitment of Raf-1.

The GTP-bound active form of Ras proteins directly binds and activates Raf-1 (14). We therefore asked whether Ras and Raf still interact in PHB depleted cells. As expected, endogenous Raf-1 interacted with Ras in EGF treated cells transfected with control siRNAs but not in untreated cells (FIG. 4B) demonstrating the activation dependent binding of Ras to Raf-1. Interestingly, the binding of Ras and Raf-1 was completely abrogated in cells lacking PHB (FIG. 4B) suggesting a direct role of PHB in the interaction of Ras and Raf-1. To confirm that PHB interferes with activation of Raf-1 by Ras we transfected constitutively active HA-Ras(G12V) in HeLa cells and either co-transfected with siPHB or control siRNAs. Interestingly, overexpressed active Ras(G12V) induced the activation of Raf-1 and ERK in control transfected cells but not in cells depleted of PHB (FIG. 4D). These results clearly show that PHB is required for the interaction of Raf-1 and Ras, a prerequisite for membrane translocation and activation of Raf-1.

We have demonstrated an unexpected role of PHB in the activation of Raf-1 by Ras. Moreover, the branch of the Ras signalling cascade controlled by PHB plays an important role in the motility of the cell. In fact, tumour cells with reduced PHB expression showed a dramatic redistribution of cadherin and β-catenin to the plasma membranes indicative of a conversion of the tumour cells from a transformed to a non-transformed phenotype (15). Moreover, prohibitin has been shown to be over expressed in gastric carcinoma, neoplastic thyroid cancer, hepatocellular carcinoma, hyperplasia, adenocarcinoma, and bladder carcinoma (16-20) indicating that prohibin may play a prominent role in the progression of neoplastic carcinoma. The facts that activating Ras mutations are found in more than 20% of all tumours (21) and that the highly conserved PHB is essential for signalling via Ras imposes PHB as a possible target for tumour therapy. One strategy could depend on the specific interference with the binding of PHB to Raf kinases in order to block activation by oncogenic Ras proteins and cellular transformation.

In one embodiment of the present invention, cancers with high expression of EGFR or Ras point mutations (pancreas, lung adenocarcinoma, colorectal, thyroid, bladder, liver and kidney) can be treated or prevented by decreasing the PHB activity in the method of the present invention for treating or/and prevention of hyperproliferative disorders. In some of these cancers, PHB is overexpressed. Since increased PHB levels are found in metastases, metastatic tumours can also be treated by decreasing PHB activity.

Subject of the present invention is also treatment of EGFR overexpressing tumours, Her-2 family overexpressing tumours, Herceptin resistant tumours, B-Raf transformed tumours, or/and Raf-1 transformed tumours. Since PHB signals downstream of EGFR and Her-2, also EGFR overexpressing tumours and Her-2 family overexpressing tumours can be treated by inhibition of PHB or/and downregulation of PHB.

Since Herceptin acts on Her-2, PHB inhibition may be an alternative treatment strategy in Herceptin resistant tumours, acting e.g. via EGFR signalling which is a path alternative to the Her-2 path.

The involvement of PHB in the signalling cascade of Raf-1 or/and B-Raf leads to the conclusion that also Raf-1 (C-Raf) transformed tumours or/and B-Raf transformed tumours can be treated by inhibition or/and downregulation of PHB.

As we have identified that reducing the activity of PHB in tumour cells block the Raf-Mapk kinase cascade directly and efficiently, RNA interference, antisense nucleic acids or/and a chemical based approach can be employed to reduce PHB expression in tumour cells in the method of the present invention for treating or/and prevention of hyperproliferative disorders.

PHB inhibition in the context of the present invention includes downregulation of PHB transcription or/and translation. While not wishing to be bound to theory, the mechanism of PHB action may be targeting of PHB to membranes combined with targeting of a Raf kinase, in particular Raf-1 (C-Raf) to membranes. Further, posttranslational modification may be important for the proper action of PHB. Therefore, PHB inhibition of the present invention also includes inhibition of targeting of PHB to membranes, inhibition of targeting of a Raf kinase, in particular Raf-1 (C-Raf) to membranes, and inhibition of posttranslational modification of PHB, in particular of posttranslational modifications required for PHB targeting to membranes or/and required for Raf kinase, in particular Raf-1 targeting to membranes.

The PHB-Raf interaction is mediated by a sequence of about 20-30 amino acids, indicating that the interaction between PHB and Raf can be interrupted with either a small molecule inhibitor or a small peptide.

In one embodiment, the inhibitor of PHB of the present invention is a nucleic acid, which can be
  i an RNA molecule capable of RNA interference,
  ii a precursor of the RNA molecule (i), or
  iii a DNA molecule encoding the RNA molecule (i) or the precursor (ii).

RNA molecules capable of RNA interference are described in WO 02/44321 which is included by reference herein.

Preferably, the inhibitor of the present invention, in particular the nucleic acid of the present invention, is used in a pharmaceutical composition.

The antibody of the present invention may be a monoclonal or polyclonal antibody, a chimeric antibody, a chimeric single chain antibody, a Fab fragment or a fragment produced by a Fab expression library.

Techniques of preparing antibodies of the present invention specific for PHB are known by a skilled person. Monoclonal antibodies may be prepared by the human B-cell hybridoma technique or by the EBV-hybridoma technique (Köhler et al., 1975, Nature 256:495-497, Kozbor et al., 1985, J. Immunol. Methods 81, 31-42, Cote et al., PNAS, 80:2026-2030, Cole et al., 1984, Mol. Cell Biol. 62:109-120). Chimeric antibodies (mouse/human) may be prepared by carrying out the methods of Morrison et al. (1984, PNAS, 81:6851-6855), Neuberger et al. (1984, 312:604-608) and Takeda et al. (1985, Nature 314:452-454). Single chain antibodies may be prepared by techniques known by a person skilled in the art.

Recombinant immunoglobulin libraries (Orlandi et al, 1989, PNAS 86:3833-3837, Winter et al., 1991, Nature 349:293-299) may be screened to obtain an antibody of the present invention which are specific against PHB. A random combinatory immunoglobulin library (Burton, 1991, PNAS, 88:11120-11123) may be used to generate an antibody with a related specifity having a different idiotypic composition.

Another strategy for antibody production is the in vivo stimulation of the lymphocyte population.

Furthermore, antibody fragments (containing F(ab')$_2$ fragments) of the present invention can be prepared by protease digestion of an antibody, e.g. by pepsin. Reducing the disulfide bonding of such F(ab')$_2$ fragments results in the Fab fragments. In another approach, the Fab fragment may be directly obtained from an Fab expression library (Huse et al., 1989, Science 254:1275-1281).

Polyclonal antibodies of the present invention may be prepared employing PHB or immunogenic fragments thereof as antigen by standard immunization protocols of a host, e.g. a horse, a goat, a rabbit, a human, etc., which standard immunization protocols are known by a person skilled in the art.

Fragments of polypeptides or/and peptides, in particular immunogenic fragments of SEQ. ID. NO:2 or a Raf kinase may have a length of at least 5 amino acid residues, preferably at least 10, more preferably at least 20 amino acid residues. The length of said fragments may be 200 amino acid residues at the maximum, preferably 100 amino acid residues at the maximum, more preferably 60 amino acid residues at the maximum, most preferably 40 amino acid residues at the maximum.

It can easily be determined by a skilled person if a gene is upregulated or downregulated. In the context of the present invention, upregulation of gene expression may be an upregulation by a factor of at least 2, preferably at least 4. Downregulation in the context of the present invention may be a reduction of gene expression by a factor of at least 2, preferably at least 4. Most preferred is essentially complete inhibition of gene expression.

"Reduction (increase) of the amount" may be a downregulation (upregulation) of gene expression by a factor of at least 2, preferably at least 4. In the case of reduction, essentially complete inhibition of gene expression is most preferred. Examples are reduction of the amount of PHB or reduction (increase) of the gene product amount of the genes of Table 1 or/and 2.

"Reduction (increase) of the activity" may be a decrease (increase) of activity of a gene or gene product by a factor of at least 2, preferably at least 4. In the case of activity reduction, essentially complete inhibition of activity is most preferred. An example relevant for the present invention is reduction of PHB activity or reduction (increase) of activity of the genes of Table 1 or/and 2.

A "target" or "target gene" for treatment of hyperproliferative disorders in the context of the present invention is a gene the expression of which is influenced by prohibitin inhibition. Prohibition inhibition may be provided by downregulation of PHB expression or by inhibition of PHB activity by an inhibitor of the present invention as discussed above.

The surprising finding of the present invention that PHB inhibition is a promising approach for treatment of hyperproliferative disorders leads to the conclusion that also genes which act downstream of PHB in the signalling cascade may be suitable targets for treatment of hyperproliferative disorders. Therefore, subject of the present invention is a method for identification of target genes for treatment of hyperproliferative disorders, based upon inhibition of PHB.

The term "target" also includes a gene product (RNA, in particular mRNA, tRNA, rRNA, a polypeptide or/and a protein) of the target gene. Preferred gene products of a target gene are selected from mRNA and a polypeptide or a protein encoded by the target gene. The most preferred gene product is a polypeptide or protein encoded by the target gene. A protein or polypeptide of the present invention may be post-translationally modified or not.

In the context of the present invention, "activity" of the gene or/and gene product includes transcription, translation, posttranslational modification, modulation of the activity of the gene product by ligand binding, which ligand may be an activator or inhibitor, etc.

In the case of PHB, "activity" also includes targeting of PHB to membranes, targeting of a Raf kinase, in particular of Raf-1 to membranes, posttranslational modification of PHB, in particular required for PHB or/and Raf kinase, in particular Raf-1 targeting to membranes.

Examples of genes which are upregulated by PHB inhibition are described in Table 1. Examples of genes which are downregulated by PHB inhibition are described in Table 2. The targets of Table 1 or/and 2 may be used for identification of new compounds for treatment or/and prophylaxis of hyperproliferative disorders. Therefore, yet another subject of the present invention is a screening method for identification of a compound suitable for treatment of a hyperproliferative disorder based upon the genes of Table 1 and 2.

The compound to be identified by the method of the present invention is a compound which increases the amount or/and the activity of the gene product of the at least one gene of Table 1 or decreases the amount or/and activity of the gene product of the at least one gene of Table 2. Therefore, the compound to be identified may be an inhibitor or an activator of a target gene or a gene product thereof.

The inhibitor or activator of a target gene or a gene product thereof may be selected from the group of nucleic acids, nucleic acid analogues such as ribozymes, peptides, polypeptides, and antibodies. A nucleic acid inhibitor or activator of a target gene or gene product thereof can be
    i an RNA molecule capable of RNA interference,
    ii a precursor of the RNA molecule (i), or
    iii a DNA molecule encoding the RNA molecule (i) or the precursor (ii).

The antibody may be an antibody specific for a gene product of a target gene, in particular an antibody specific for a polypeptide or protein encoded by a target gene. Production of a suitable antibody is described above in the context of prohibitin.

The inhibitor or activator of a target gene or gene product thereof may be used for the manufacture of a pharmaceutical composition for treatment or/and prophylaxis of a hyperproliferative disorder.

In the method of the present invention for identification of a compound suitable for treatment of a hyperproliferative disorder based upon the genes of Table 1 and 2, preferably employed are genes listed in Table 1 and 2 involved in cancer signalling, angiogenesis, adhesion, invasion or/and metastasis formation.

Most preferred genes listed in Table 1 and 2 are genes involved in cancer signalling: NM_004419, DUSP5 dual specificity phosphatase 5, direct target of p53; U21049, DD96, epithelial protein up-regulated in carcinoma, membrane associated protein 17; NM_005130 HBP17 (heparin-binding growth factor binding protein), which binds to HB-EGF which activates the RAS-signaling pathway.

Further most preferred genes listed in Table 1 and 2 are genes encoding angiogenis factors: NM_003370, VASP, vasodilator-stimulated phosphoprotein, direct angiogenic activity, which plays also a role in cell motility and metastasis formation; NM_139314, ANGPTL4, *Homo sapiens* angiopoietin-like 4 (ANGPTL4), transcript variant 1; NM_006108, SPON1, *Homo sapiens* spondin 1, extracellular matrix protein (SPON1), having a potential function as an angiopoietin or/and as spondin.

Further most preferred genes listed in Table 1 and 2 are genes involved in adhesion, invasion and metastasis: NM_003255, TIMP2, tissue inhibitor of metalloproteinase 2, which plays an important role in invasion and metastasis formation by inhibiting metalloproteases; NM_006108, SPON1, *Homo sapiens* spondin 1, extracellular matrix protein (SPON1); NM_000213, ITGB4, integrin beta 4, Extracellular matrix binding and signaling, plays an important role in adhesion and invasion; NM_012385 P8, p8 protein (candidate of metastasis 1); NM_004360, CDH1, cadherin 1, type 1, E-cadherin (epithelial), plays an important role in adhesion and invasion as a protein involved in cell-cell contact formation; NM_017717, MUCDHL, mucin and cadherin-like; NM_005130 HBP17 (heparin-binding growth factor binding protein), which binds to HB-EGF which activates the RAS-signaling pathway; NM_002272, KRT4, *Homo sapiens* keratin 4 (KRT4), which is involved in adhesion and wound healing; NM_004363 CEACAM5 (*Homo sapiens* carcinoembryonic antigen-related cell adhesion molecule 5) and NM_002483 CEACAM6 (carcinoembryonic antigen-related cell adhesion molecule 6). Carcinoembryonic antigen (CEA) is one of the most frequently used serum tumor markers for carcinoma, particularly in colorectal cancer. The role of CEACAM in tumor growth is complex, with apparently conflicting effects on tumor growth seen in different tumor models. Studies in breast and prostate cancer models suggest that CEACAM may be a tumor suppression gene, whereas other models suggest CEACAM may be involved in tumor invasion and metastasis.

The invention is further illustrated by the following figures, tables and examples.

FIGURE AND TABLE LEGENDS

FIG. 1: Knock down of prohibitin induces changes in epithelial cell morphology. Transfection of siPHB reduces the mRNA level (A) and the protein level (B) of prohibitin compared to control transfections (siLuc or siGFP, respectively). Knock down of prohibitin (siPHB) induces the aggregation and reduced migration of epithelia cancer cells not seen in control cells (siGFP) (C). Transfection of siPHB-3 reduces the PHB mRNA (D) and protein level (E). Expression of the cloned PHB gene pPHB-c in siPHB-3 transfected cells restores PHB expression. PHB-c harbours a N-terminal Flag-tag and has therefore a slightly increased molecular mass compared to endogenous PHB. Expression of the cloned prohibitin pPHB-c in siPHB-3 transfected cells prevents cell cluster formation. For details, see Materials and Methods.

FIG. 2: Knock down of prohibitin induces the formation of adherens junctions and changes in epithelial morphogenesis. Knock down of prohibitin (siPHB) induces the formation of multilayered epithelial cell clusters (A, B) whereas control cells (siLuc) form monolayers (C,D). Samples were analyzed by scanning (SEM, A+C) and transmission electron microscopy (TEM, B+D).

Confocal immunofluorescence analysis of prohibitin knock down cells (E, F, G) and controls (H, I, J). Cells with reduced prohibitin expression show a strong membrane staining for pan-cadherin (E) and β-catenin (F) while staining of control cells reveals a reduced membrane signal and a diffuse cytoplasmic pattern (H, I). G and J show the respective overlays including a DNA stain. G', J' and G",J" are XZ and YZ reconstructions of confocal Z stacks. The reconstructions clearly reveal that the cell clusters of prohibitin knock down cells are multilayered. Induction of cell migration on collagen by EGF is impaired in prohibitin knock down cells. Shown are the individual frames from various time points of a time-lapse video on the control and prohibitin knock down cells with EGF.

FIG. 3:
Prohibitin is Required During EGF Induced Raf-MAPK Activation

Hela cells transfected with control siRNA (siLam), siHer-2 and siPHB were treated with EGF and the phosphorylation of ERK, AKT (A) and Raf-1 (B) was determined by immunoblot analysis with phospho-specific antibodies. Complementation of siPHB transfected HeLa cells restores Raf-1 activation (D). Shown are the levels of Raf-1 pS259 and Raf-1 pS338 blots revealing an increase in Raf-1 pS259 phosphorylation in cells transfected with siPHB-3 (D).

Addition of Phorbol ester (PMA) leads to rapid resolution of cell clusters and the activation of ERK irrespective of PHB levels (E, F). Shown are different time points from a time lapse microscopy of siPHB transfected cells treated with PMA (E). Co-expression of constitutively active RafBXB (G,H) or the cloned PHB gene restore ERK activation and cell cluster formation in siPHB transfected cells.

FIG. 4:

PHB is Required for the Activation of Raf-1 by Ras.

Prohibitin and Raf-1 were found in the caveolin rich fraction of the plasma membrane in cells with normal prohibitin expression (A; siLuc). Raf-1 is lost from the caveolae in cells with reduced levels of PHB (A; siPHB). The different fractions and the respective concentration of sucrose obtained after gradient centrifugation are indicated. Caveolin-1 (Cav-1) as marker for caveolae as well as PHB and Raf-1 were detected by immuno blotting. Ras-Raf-1 interaction is impaired in PHB knock down cells (B). HeLa cells transfected with control siRNA (siLuc) or siPHB were treated with or without EGF. Ras was then immunoprecipitated using pan-Ras antibody and co-precipitating Raf-1 was detected by immunoblotting (IP). Amounts of PHB and Raf-1 were verified in the whole cell lysates (lysate). Active Ras fails to activate Raf-1 and ERK in PHB knock down cells (D). HeLa cells transfected with control siRNA (siLuc) or siPHB and expression plasmids for H-Ras or H-Ras(G12V) were treated with EGF or buffer. Activation of Raf-1 and ERK was tested by immunoblot analysis using phoshpo-specific antibodies as indicated. Expression of Ras constructs was verified by using anti-HA tag antibody.

FIG. 5:

Nucleotide Sequence encoding PHB (GenBank-Accession-No. NM_002634, SEQ. ID. NO:1). The coding region is given in bold letters.

FIG. 6:

Amino acid sequence of PHB (GenBank-Accession-No. NM_002634, SEQ. ID. NO:2).

Figure 7:
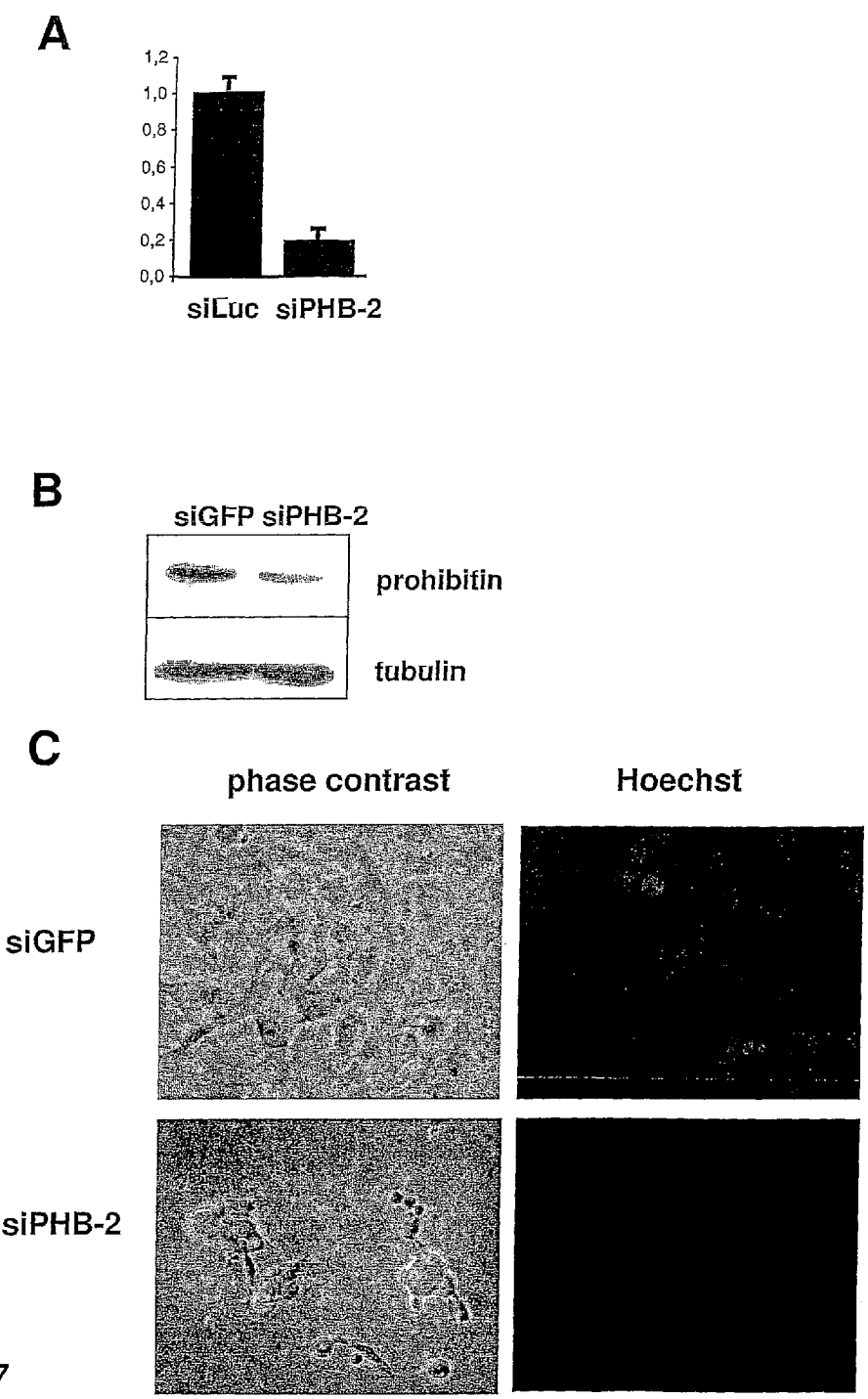

FIGS. 7A, B and C: Formation of cell clusters as consequence of silencing PHB expression in HEp-2 cells. Transfection of siPHB-2 reduces the mRNA level (A) and the protein level (B) of prohibitin compared to control transfections (siLuc or siGFP, respectively). Knock down of prohibitin (siPHB-2) induces the aggregation and multilayered organisation of HEp-2 cells not seen in control cells (siGFP) (C).

Figure 8:
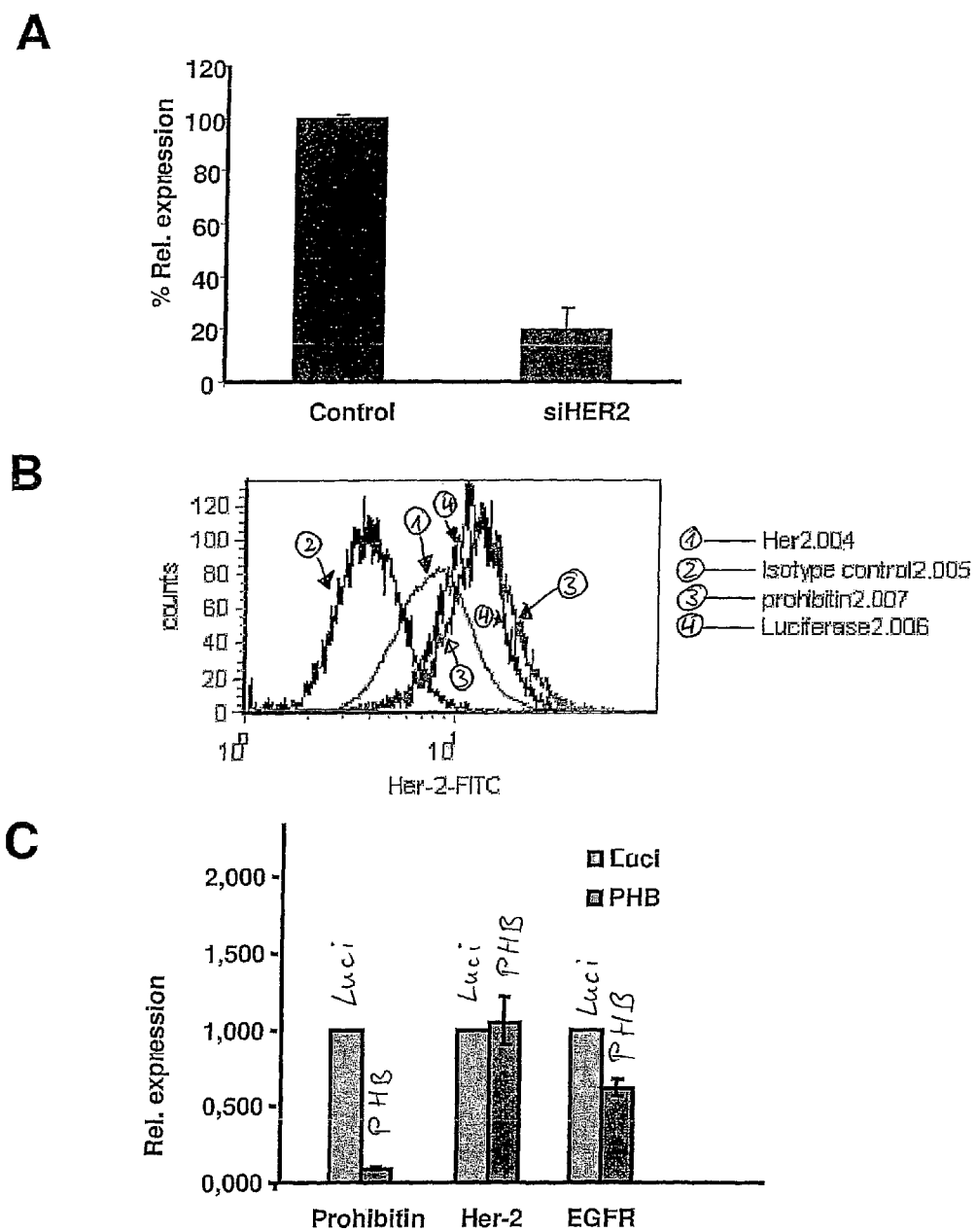
Figure 8:
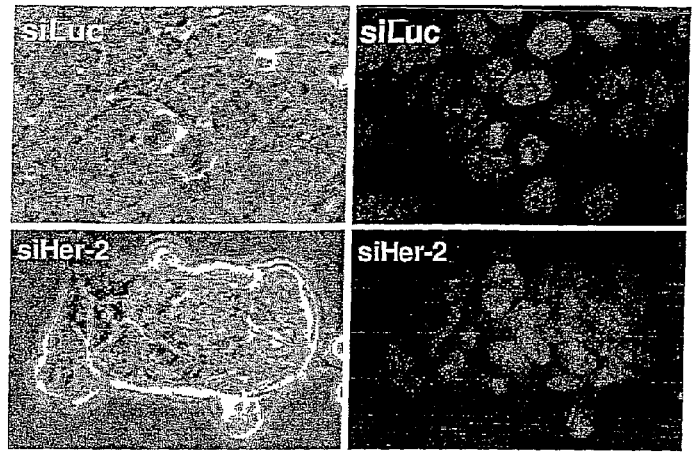

FIGS. 8A, B, C and D: Knock Down of Her-2 Results in the Formation of Cell Clusters.

Validation of siHer-2 by quantitative realtime PCR indicates reduced Her-2 mRNA levels of about 80% of control (siLuc) (A). Transfection of siHer-2 induces the formation of cell clusters (B). Transfection of siHer-2 but not of siPHB reduces the surface exposure of Her-2 (C). Shown is a FACS analysis of cells transfected with siHer-2 (No. 1), siPHB (No. 3) or siLuc (No. 4). Cells were stained with anti-Her-2 antibody (Nos. 1, 3, 4) or a isotype control (No. 2). Relative expression of prohibitin, Her-2 and EGFR in cells transfected with siLuc (Luci) or siPHB (PHB) (D).

Figure 9:
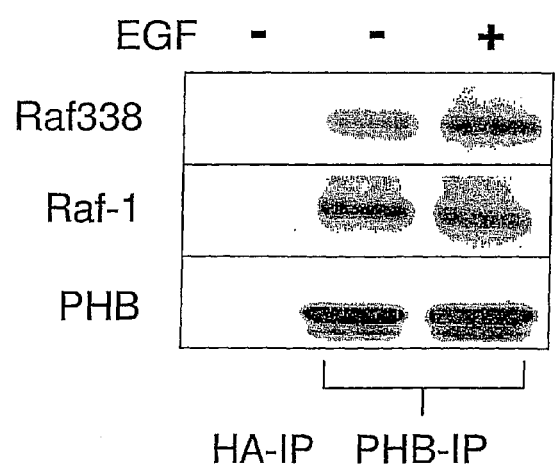

FIG. 9: Endogenous Raf-1 Interacts with PHB

Endogenous PHB was precipitated from EGF or buffer treated HeLa cells and co-precipitating Raf-1 was determined. Raf-1 and Raf-1 pS338 strongly interact with PHB. IP with HA-antibody was used as an isotype control.

Table 1: Genes up-regulated in prohibitin depleted cells

Table 2: Genes down-regulated in prohibitin depleted cells

EXAMPLE 1

Materials and Methods

Cell Culture

HeLa cells, HEp-2 cells, AGS cells were cultured in RPMI-1640 medium supplemented with 10% fetal calf serum (Gibco BRL, Karlsruhe, Germany), and penicillin (100 U/ml)/streptomycin (100 µg/ml) (Gibco BRL, Karlsruhe, Germany) at 37° C. in 5.0% $CO_2$. Cells were serum starved for 4-6 h prior to the addition of EGF (Promocell) at a final concentration of 20 ng/ml. MEK-1 inhibitor PD98059 was purchased from (Calbiochem).

Transfection of siRNAs

In order to silence expression of prohibitin, 50,000 cells/well were seeded in a 12 well plate at least 20 h prior to transfection. siRNAs were transfected using the Transmessenger transfection kit and RNAifect transfection kit (Qiagen). Two days post transfection, the nearly confluent cells were trypsinized and one half of the cells was seeded on glass cover slips in a 12 well plate for immunofluorescence analysis while the other half was used for western blot analysis. The following siRNAs were employed in this study:

```
                                          (SEQ. ID. NO: 3)
siGFP 5'-AAGUUCAGCGUGUCCGGCGAG-3', (SEQ. ID. NO: 4)
siLuc-5'-AACUUACGCUGAGUACUUCGA-3', (SEQ. ID. NO: 5)
siPHB 5'UGUCAACAUCACACUGCGCdTdT3'
and (SEQ. ID. NO: 6)
GCGCAGUGUGAUGUUGACAdTdT (SEQ. ID. NO: 7)
siPHB-2 AGCCAGCTTCCTCGCATCTdTdT,
and (SEQ. ID. NO: 8)
AGATGCGAGGAAGCTGGCTdGdG, (SEQ. ID. NO: 9)
siPHB-3 5'-CCCAGAAAUCACUGUGAAAdTdT-3',
and (SEQ. ID. NO: 10)
TTTCACAGUGAUUUCUGGGdTdT.
```

For complementation experiments, cells grown to 80% confluence were transfected with the siPHB-3 siRNA (80 nM) and the full length PHB open reading frame cloned in pcDNA3-myc vector (0.5 µg) or the RafBxB construct (0.5 µg) (a kind gift from Ulf Rapp) using RNAifect transfection kit as mentioned before. The control cells were transfected with the empty vector and a siRNA directed against luciferase (siLuc).

Validation of mRNA Levels by Quantitative Realtime PCR 20,000 cells/well were seeded in a 96 well plate one day prior to transfection. Transfection was performed with 0.25 µg siRNA directed against PHB and Luciferase as control and 2 µl Transmessenger per well according to manufacturer's instructions. After 48 h, RNA was isolated using the RNeasy® 96 BioRobot® 8000 system (Qiagen). The relative amount of PHB mRNA was determined by real time PCR using Quantitect™ SYBR® Green RT-PCR Kit from Qiagen following manufacturer's instructions. The expression level of PHB mRNA was normalized against the internal standard GAPDH. The following primers were used:

PHB-5': 5'-CTTTGACTGCCGTTCTCGAC-3', (SEQ. ID. NO: 11)

PHB-3': 5'-TGGGTGGATTAGTTCTCCAGC-3', (SEQ. ID. NO: 12)
and

GAPDH-5': 5'-GGTATCGTGGAAGGACTCATGAC-3', (SEQ. ID. NO: 13)

GAPDH-3': 5'-ATGCCAGTGAGCTTCCCGTTCAG-3'. (SEQ. ID. NO: 14)

Preparation of Caveolae Rich Fractions

Detergent extraction and floatation were performed as described previously (22). Shortly, ME-180 or HeLa cells transfected with siRNAs were solubilized in 1% Triton X-100, MBS [Mes-buffered saline; 0.25 M NaCl and 25 mM Mes (pH 6.8)] and a cocktail of protease inhibitors on ice for 1 h without agitation. The cell lysates were adjusted to 45% sucrose in MBS, overlaid with 7 ml of 35% and 2 ml 5% sucrose in MBS, and centrifuged for 18 h at 36,000 rpm in a SW40Ti rotor (Beckman Instruments). Twelve 1 ml fractions were collected from the top of the gradient and were assayed for protein content, caveolin-1, Raf-1, Ras and prohibitin.

SDS-PAGE and Western Blot

For SDS-PAGE, cells were lysed in single detergent buffer (20 mM Tris-HCl pH 7.5, 150 mM NaCl, 1% NP-40, 1 µgml$^{-1}$ Aprotinin, 0.5 µgml$^{-1}$ Leupeptin, 1 mM Pefabloc, 10 µM Pepstatin) for 15-20 min on ice and sonicated twice for 15 sec. Lysates were cleared by centrifugation for 10 min at 13,000 rpm, Sample buffer was added to these lysates and boiled at 90° C. for 2 min before loading onto the gels. After separation the proteins were transferred to PVDF-membranes. For immunoblot analysis membranes were blocked with 3% BSA in TBS with 0.5% Tween-20 for 2 h and incubated with anti-prohibitin (Neomarkers), anti-alpha tubulin antibody (Sigma), anti-E-cadherin (Zymed labs), anti-Pan-cadherin (Sigma) or anti-beta-catenin (Sigma) anti-caveolin (N20, Santa Cruz Biotechnology), c-Raf rabbit polyclonal antibody (Santa Cruz Biotechnology), c-Raf mouse monoclonal antibody (Pharmingen), Caveolin mouse monoclonal antibody, anti-Raf-1 pS338 and anti-Raf-1 pS259 rabbit monoclonal antibody (Cell signalling), phospho-MEK (Cell signalling), anti-beta actin monoclonal antibody (Sigma), anti-Her-2 rabbit polyclonal antibody from (Cell signalling) (anti-pan-Ras monoclonal antibody (Pharmingen), phosphor-ERK, Anti-ERK2 antibody, EGFR-antibody and anti-Myc 9E10 mouse monoclonal antibody (Santa Cruz). Antigen antibody complexes were detected by horseradish peroxidase coupled antibodies (Pharmingen) followed by enhanced chemiluminescence (NEN).

FACS Analysis

For surface staining of Her-2, Hela cells transfected with siRNAs were detached by Accutase treatment 60 h post transfection. The cells were washed once with PBS and incubated in PBS with 2% BSA for 20 min at room temperature. The cells were once again washed with PBS and stained with FITC coupled anti-Her-2 antibody (Bender med systems) diluted in BSA containing PBS at a final dilution of 1:50 and incubated at room temperature for 40 min. At the end of the incubation the cells were washed twice with PBS and the labelled cells were detected using a Becton Dickinson flow cytometer.

Immunoprecipitation

Cells were washed in ice cold PBS and lysed in RIPA buffer containing 20 mM Tris-HCl pH 7.5, 150 mM NaCl, 0.5% NP-40, 0.5% Triton X-100, 1 mM NaVO$_3$, 10 mM Na-pyrophosphate, 1 mM NaF, 0.5 mM EDTA, 0.5 mM EGTA, 1 mM DTT, 1 µg/ml Aprotinin, 0.5 µg/ml Leupeptin, 1 mM Pefabloc, 10 µM Pepstatin for 30 min on ice and sonicated twice for 10 sec. Lysates were cleared by centrifugation for 15 min at 13,000 rpm. Supernatants were incubated with agarose-coupled anti-H-Ras (Santa Cruz Biotechnology) or Raf-1 (C-12, Santa Cruz Biotechnology) for over night. In the latter case the antigen-antibody complexes were pull down by Sepharose coupled protein A/G beads.

In Vitro Kinase Assay

For in vitro kinase assays, Hela cells transfected with siRNAs were treated with or without EGF and cell lysates were prepared for immunoprecipitations as mentioned before. The immunoprecipitated Raf-1 was washed twice with RIPA buffer and kinase buffer w/o ATP (25 mM Hepes-NaOH pH 7.5, 5 mM MgCl$_2$, 4 mM MnCl$_2$). The beads were incubated at 30° for 30 min in the presence of [γ-$^{32}$P] ATP in kinase buffer supplemented with 30 µM ATP with or without 2 µg of MEK-1 full length protein (Santa Cruz) in a total volume of 40 µl. Kinase reactions were terminated by addition of SDS sample buffer and boiling. The proteins were separated by SDS-PAGE and analyzed by autoradiography.

Transmission Electron Microscopy siRNA transfected Hela cells were trypsinized and seeded on glass coverslips at 48 h post transfection. After 60 h, cells were fixed with 2.5% glutaraldehyde, postfixed with 0.5% osmium tetroxide and contrasted using tannic acid and uranyl acetate. Specimens were dehydrated in a graded ethanol series and embedded in Polybed. Ultrathin sections were analysed in a Leo 906E transmission electron microscope (Leo Oberkochen).

Scanning Electron Microscopy

Samples grown on glass coverslips were fixed in 2.5% glutaraldehyde, dehydrated in a graded ethanol series, critical-point dried and coated with a layer of 2 nm platinum/carbon. Specimens were analysed in a Leo 1550 field emission scanning electron microscope (Leo, Oberkochen).

Immunofluorescence Microscopy siRNA transfected cells were seeded on glass coverslips at 48 h post transfection and fixed with 4% PFA/PBS at 60 h post transfection. The fixed cells were washed once with PBS and permeabilised with 1% Triton/PBS for 1 min and blocked (1% BSA, 5% NGS, 0.05% Tween 20 in PBS for 1 h. The samples were incubated with antibodies against Pan-Cadherin (Sigma) and ?-Catenin (Sigma) in blocking buffer. After washing, bound antibodies were detected using goat anti-mouse Cy2 and goat anti rabbit Cy3 secondary antibodies. Nuclei were stained with Draq 5 (Bilostatus LTD). Tri colour Z-stacks were generated using a Leica TCS-SP confocal microscope (Leica Microsystems). For 3-dimensional analysis, stacks were processed using Volocity software (Improvision).

EXAMPLE 2

Microarray Method

In a microarray analysis, target genes were identified which are downregulated or upregulated in prohibitin depleted cells. Results are summarized in Tables 1 and 2.

Microarray experiments were carried out as two-color dye-reversal ratio hybridizations on a 44.000 Whole Human Genome Oligo Microarray AMADID 012391 with 37327 records and 43931 features (Agilent Technologies, Palo Alto, Calif., USA). RNA labeling was performed with a Fluorescent Linear Amplification Kit (Agilent Technologies). In brief, cDNA was reverse transcribed from 4 µg total RNA with an oligo-dT-T7 promoter primer and MMLV-RT. Second strand synthesis was carried out with random hexamers. Fluorescent anti-sense cRNA was synthesized with either cyanine 3-CTP (Cy3-CTP) or cyanine 5-CTP (Cy5-CTP) and T7 polymerase. The fluorescent-labeled anti-sense cRNA was precipitated over night with LiCl, ethanol washed and resuspended in water. The purified products were quantified at $A_{552nm}$ for Cy3-CTP and $A_{650nm}$ for Cy5-CTP and labeling efficiency was verified with a Nanodrop photometer (Kisker, Steinfurt, Germany). Before hybridization, 1.25 µg labeled cRNA of each product were fragmented and mixed with control targets and hybridization buffer according to the supplier's protocol (Agilent Technologies). Hybridizations were done over night for approximately 17 h at 60° C. The slides were washed according to the manufacturer's manual and scanning of microarrays was performed with 5 µm resolution using a DNA microarray laser scanner (Agilent Technologies). In order to compensate dye specific effects, and to ensure statistically relevant data (G. A. Churchill, Fundamentals of experimental design for cDNA microarrays, Nat Genet. 32 Suppl (2002) 490-495), a color swap dye reversal was performed. Features were extracted with an image analysis tool Version A 6.1.1 (Agilent Technologies) using default settings. Data analysis was carried out on the Rosetta Inpharmatics platform Resolver Built 4.0. Ratio profiles were generated from raw scan data by a processing pipeline which includes pre-processing (Feature Extraction) and post-processing (Rosetta Resolver) of data and error model adjustments to the raw scan data. Ratio profiles were combined in an error-weighted fashion (Rosetta Resolver) to create ratio experiments, and ratio experiments consisted of one or more ratio profiles. Expression patterns were identified using stringent analysis criteria of 2-fold expression cut-offs of the ratio experiments and an anti-correlation of the dye reversal ratio profiles. Anti-correlation was determined by using the 'compare function' to match two color-swap dye-reversal hybridizations and to decide how similar or dissimilar they were. In this way, only anti-correlated spots that had on the one array a red colour and on the other one a green colour and vice versa were selected. We compared color-swap dye-reversal hybridizations of individual 2 two-channel hybridizations resulting in unchanged genes, query signature genes, target signature genes, common signature genes and anti-correlated genes. By combining the first and the second criteria of analysis we filtered out data points with low P-value (P-value<0.01), making the analysis robust and reproducible. Additionally, by using this strategy we did the data selection independent of error models implemented in the Rosetta Resolver system.

REFERENCE LIST

1 McClung, J. K., Jupe, E. R., Liu, X. T. & Dell'Orco, R. T. Prohibitin: potential role in senescence, development, and tumor suppression. Exp. Gerontol. 30, 99-124 (1995).

2 Harari, D. & Yarden, Y. Molecular mechanisms underlying ErbB2/HER2 action in breast cancer. Oncogene 19, 6102-6114 (2000).

3 Gschwind, A., Fischer, O. M. & Ullrich, A. The discovery of receptor tyrosine kinases: targets for cancer therapy. Nat. Rev. Cancer 4, 361-370 (2004).

4 Spencer, K. S., Graus-Porta, D., Leng, J., Hynes, N. E. & Klemke, R. L. ErbB2 is necessary for induction of carcinoma cell invasion by ErbB family receptor tyrosine kinases. J. Cell Biol. 148, 385-397 (2000).

5 Klemke, R. L. et al. Regulation of cell motility by mitogen-activated protein kinase. J. Cell Biol. 137, 481-492 (1997).

6 Downward, J. Targeting RAS signalling pathways in cancer therapy. Nat. Rev. Cancer 3, 11-22 (2003).

7 Dhillon, A. S., Meikle, S., Yazici, Z., Eulitz, M. & Kolch, W. Regulation of Raf-1 activation and signalling by dephosphorylation. EMBO J. 21, 64-71 (2002).

8 Howe, L. R. et al. Activation of the MAP kinase pathway by the protein kinase raf. Cell 71, 335-342 (1992).

9 Bruder, J. T., Heidecker, G. & Rapp, U. R. Serum-, TPA-, and Ras-induced expression from Ap-1/Ets-driven promoters requires Raf-1 kinase. Genes Dev. 6, 545-556 (1992).

10 Leevers, S. J., Paterson, H. F. & Marshall, C. J. Requirement for Ras in Raf activation is overcome by targeting Raf to the plasma membrane. Nature 369, 411-414 (1994).

11 Marais, R., Light, Y., Paterson, H. F. & Marshall, C. J. Ras recruits Raf-1 to the plasma membrane for activation by tyrosine phosphorylation. EMBO J. 14, 3136-3145 (1995).

12 Prior, I. A. et al. GTP-dependent segregation of H-ras from lipid rafts is required for biological activity. Nat. Cell Biol. 3, 368-375 (2001).

13 Wang, S., Nath, N., Fusaro, G. & Chellappan, S. Rb and prohibitin target distinct regions of E2F1 for repression and respond to different upstream signals. Mol. Cell. Biol. 19, 7447-7460 (1999).

14 Shields, J. M., Pruitt, K., McFall, A., Shaub, A. & Der, C. J. Understanding Ras: 'it ain't over 'til it's over'. Trends Cell Biol. 10, 147-154 (2000).

15 Hirohashi, S. & Kanai, Y. Cell adhesion system and human cancer morphogenesis. Cancer Sci. 94, 575-581 (2003).

16 Wang, K. J., Wang, R. T. & Zhang, J. Z. Identification of tumor markers using two-dimensional electrophoresis in gastric carcinoma. World J. Gastroenterol. 10, 2179-2183 (2004).

17 Srisomsap, C. et al. Detection of cathepsin B up-regulation in neoplastic thyroid tissues by proteomic analysis. Proteomics. 2, 706-712 (2002).

18 Seow, T. K. et al. Two-dimensional electrophoresis map of the human hepatocellular carcinoma cell line, HCC-M, and identification of the separated proteins by mass spectrometry. Electrophoresis 21, 1787-1813 (2000).

19 Byrjalsen, I. et al. Two-dimensional gel analysis of human endometrial proteins: characterization of proteins with increased expression in hyperplasia and adenocarcinoma. Mol. Hum. Reprod. 5, 748-756 (1999).

20 Asamoto, M. & Cohen, S. M. Prohibitin gene is overexpressed but not mutated in rat bladder carcinomas and cell lines. Cancer Lett. 83, 201-207 (1994).

21 Bos, J. L. ras oncogenes in human cancer: a review. Cancer Res. 49, 4682-4689 (1989).

22 Smart, E. J., Foster, D. C., Ying, Y. S., Kamen, B. A. & Anderson, R. G. Protein kinase C activators inhibit receptor-mediated potocytosis by preventing internalization of caveolae. J. Cell Biol. 124, 307-313 (1994).

The invention claimed is:

1. A method for reducing hyper activation of the Ras-MAPK cascade by inhibition of prohibitin over-expression in a patient in need of such treatment, comprising administering to said patient a therapeutically effective amount of a compound which inhibits Prohibitin (PHB) together with pharmaceutically acceptable carriers, adjuvants, diluents or/and additives.

2. The method as claimed in claim 1, wherein said patient is suffering from metastatic tumors, benign tumors, carcinoma, neoplastic carcinoma, gastric carcinoma, larynx carcinoma, neoplastic thyroid cancer, hepatocellular carcinoma, hyperplasia, adenocarcinoma, bladder carcinoma, EGFR overexpressing tumors, Her-2 family overexpressing tumors, Herceptin resistant tumors, B-Raf transformed tumors, or/and Raf-1 transformed tumors.

3. The method as claimed in claim 1, wherein the compound which inhibits Prohibitin (PHB), specifically inhibits the interaction of PHB with a Raf kinase.

4. The method as claimed in claim 3, wherein the compound which inhibits Prohibitin (PHB), specifically inhibits the binding of PHB to a Raf kinase.

5. The method according to claim 4, wherein said Raf kinase is Raf-1.

6. The method as claimed in claim 1, wherein the compound which inhibits Prohibitin (PHB) inhibits activation of the Ras-Raf signalling pathway.

7. The method as claimed in claim 1, wherein the compound which inhibits Prohibitin (PHB) specifically disrupts a Ras-Raf interaction.

8. The method as claimed in claim 1, wherein the compound which inhibits Prohibitin (PHB) inhibits downstream of members of the EGFR family.

9. The method as claimed in claim 1, wherein the compound which inhibits Prohibitin (PHB) converts tumor cells from a transformed to a non-transformed phenotype in vitro and in vivo.

10. The method as claimed in claim 1, wherein the compound which inhibits Prohibitin (PHB) prevents angiogenesis in tumors.

11. The method as claimed in claim 1, wherein the compound which inhibits Prohibitin (PHB) prevents cell migration in vitro or/and in vivo.

12. The method as claimed in claim 1, wherein the compound which inhibits Prohibitin (PHB) down regulates PHB transcription or/and translation, inhibits targeting of PHB to membranes, inhibits targeting of a Raf kinase, or/and inhibits posttranslational modification of PHB.

13. The method as claimed in claim 1, wherein the at least one inhibitor is selected from the group of nucleic acids, nucleic acid analogues, peptides, polypeptides, and antibodies.

14. The method as claimed in claim 13, wherein the nucleic acid is selected from the group consisting of
(i) an RNA molecule capable of RNA interference,
(ii) a precursor of the RNA molecule (i), and
(iii) a DNA molecule encoding the RNA molecule (i) or the precursor (ii).

15. The method as claimed in claim 14, wherein the DNA molecule is a vector.

16. The method as claimed in claim 1, wherein the nucleic acid is a double-stranded RNA molecule with or without a single-stranded overhang alone at one end or at both ends.

17. The method according to claim 6, wherein the compound which inhibits Prohibitin (PHB) inhibits activation of the Ras-Raf-MAPK pathway or/and the PHB dependent branch of the Ras signalling pathway.

18. The method according to claim 8, wherein the compound which inhibits Prohibitin (PHB) inhibits downstream of EGFR and Her-2.

19. The method according to claim 12, wherein the compound which inhibits Prohibitin (PHB) inhibits targeting of Raf-1 (C-Raf) to membranes.

20. The method according to claim 12, wherein the compound which inhibits Prohibitin (PHB) inhibits posttranslational modification of PHB required for the PHB targeting to membranes or/and required for the targeting of a Raf kinase.

21. The method according to claim 20, wherein the compound which inhibits Prohibitin (PHB) inhibits posttranslational modification of PHB required for the targeting of Raf-1 (C-Raf) to membranes.

22. The method according to claim 13, wherein the nucleic acid analogue is a ribozyme.

23. The method as claimed in claim 16, wherein the double-stranded RNA molecule is a double-stranded siRNA molecule.

24. The method according to claim 1, wherein said compound which inhibits Prohibitin is selected from the group consisting of nucleic acids, nucleic acid analogues, antibodies, peptides and polypeptides, wherein said peptides and polypeptides are immunogenic fragments of SEQ ID NO:2 or a Raf kinase and have a length of at least 5 amino acid residues.

25. The method according to claim 1, wherein said compound which inhibits Prohibitin is selected from the group consisting of siRNAs, small molecules, and antibodies.

* * * * *

SEQUENCE LISTING

<160> NUMBER OF SEQ ID NOS: 14

<210> SEQ ID NO 1
<211> LENGTH: 1826
<212> TYPE: DNA
<213> ORGANISM: human
<220> FEATURE:
<221> NAME/KEY: CDS
<222> LOCATION: (74)..(892)

<400> SEQUENCE: 1

```
agtatgtgtg gttggggaat tcatgtggag gtcagagtgg aagcaggtgt gagagggtcc      60
agcagaagga aac atg gct gcc aaa gtg ttt gag tcc att ggc aag ttt        109
            Met Ala Ala Lys Val Phe Glu Ser Ile Gly Lys Phe
            1               5                   10 ggc ctg gcc tta gct gtt gca gga ggc gtg gtg aac tct gcc tta tat      157
Gly Leu Ala Leu Ala Val Ala Gly Gly Val Val Asn Ser Ala Leu Tyr
        15                  20                  25 aat gtg gat gct ggg cac aga gct gtc atc ttt gac cga ttc cgt gga      205
Asn Val Asp Ala Gly His Arg Ala Val Ile Phe Asp Arg Phe Arg Gly
    30                  35                  40 gtg cag gac att gtg gta ggg gaa ggg act cat ttt ctc atc ccg tgg      253
Val Gln Asp Ile Val Val Gly Glu Gly Thr His Phe Leu Ile Pro Trp
45                  50                  55                  60 gta cag aaa cca att atc ttt gac tgc cgt tct cga cca cgt aat gtg      301
Val Gln Lys Pro Ile Ile Phe Asp Cys Arg Ser Arg Pro Arg Asn Val
                65                  70                  75 cca gtc atc act ggt agc aaa gat tta cag aat gtc aac atc aca ctg      349
Pro Val Ile Thr Gly Ser Lys Asp Leu Gln Asn Val Asn Ile Thr Leu
            80                  85                  90 cgc atc ctc ttc cgg cct gtc gcc agc cag ctt cct cgc atc ttc acc      397
Arg Ile Leu Phe Arg Pro Val Ala Ser Gln Leu Pro Arg Ile Phe Thr
        95                 100                 105 agc atc gga gag gac tat gat gag cgt gtg ctg ccg tcc atc aca act      445
Ser Ile Gly Glu Asp Tyr Asp Glu Arg Val Leu Pro Ser Ile Thr Thr
    110                 115                 120 gag atc ctc aag tca gtg gtg gct cgc ttt gat gct gga gaa cta atc      493
Glu Ile Leu Lys Ser Val Val Ala Arg Phe Asp Ala Gly Glu Leu Ile
125                 130                 135                 140 acc cag aga gag ctg gtc tcc agg cag gtg agc gac gac ctt aca gag      541
Thr Gln Arg Glu Leu Val Ser Arg Gln Val Ser Asp Asp Leu Thr Glu
                145                 150                 155 cga gcc gcc acc ttt ggg ctc atc ctg gat gac gtg tcc ttg aca cat      589
Arg Ala Ala Thr Phe Gly Leu Ile Leu Asp Asp Val Ser Leu Thr His
            160                 165                 170 ctg acc ttc ggg aag gag ttc aca gaa gcg gtg gaa gcc aaa cag gtg      637
Leu Thr Phe Gly Lys Glu Phe Thr Glu Ala Val Glu Ala Lys Gln Val
        175                 180                 185 gct cag cag gaa gca gag agg gcc aga ttt gtg gtg gaa aag gct gag      685
Ala Gln Gln Glu Ala Glu Arg Ala Arg Phe Val Val Glu Lys Ala Glu
    190                 195                 200 caa cag aaa aag gcg gcc atc atc tct gct gag ggc gac tcc aag gca      733
Gln Gln Lys Lys Ala Ala Ile Ile Ser Ala Glu Gly Asp Ser Lys Ala
205                 210                 215                 220 gct gag ctg att gcc aac tca ctg gcc act gca ggg gat ggc ctg atc      781
Ala Glu Leu Ile Ala Asn Ser Leu Ala Thr Ala Gly Asp Gly Leu Ile
                225                 230                 235 gag ctg cgc aag ctg gaa gct gca gag gac atc gcg tac cag ctc tca      829
Glu Leu Arg Lys Leu Glu Ala Ala Glu Asp Ile Ala Tyr Gln Leu Ser
            240                 245                 250
```

```
cgc tct cgg aac atc acc tac ctg cca gcg ggg cag tcc gtg ctc ctc      877
Arg Ser Arg Asn Ile Thr Tyr Leu Pro Ala Gly Gln Ser Val Leu Leu
        255                 260                 265 cag ctg ccc cag tga gggcccaccc tgcctgcacc tccgcgggct gactgggcca      932
Gln Leu Pro Gln
    270 cagccccgat gattcttaac acagccttcc ttctgctccc accccagaaa tcactgtgaa     992
atttcatgat tggcttaaag tgaaggaaat aaaggtaaaa tcacttcaga tctctaatta   1052
gtctatcaaa tgaaactctt tcattcttct cacatccatc tactttttta tccacctccc   1112
taccaaaaat tgccaagtgc ctatgcaaac cagctttagg tcccaattcg gggcctgctg   1172
gagttccggc ctgggcacca gcatttggca gcacgcaggc ggggcagtat gtgatggact   1232
ggggagcaca ggtgtctgcc tagatccacg tgtggcctcc gtcctgtcac tgatggaagg   1292
tttgcggatg agggcatgtg cggctgaact gagaaggcag gcctccgtct tcccagcggt   1352
tcctgtgcag atgctgctga agagaggtgc cggggagggg cagagaggaa gtggtctgtc   1412
tgttaccata gtctgattc tctttaactg tgtgaccagc ggaaacaggt gtgtgtgaac    1472
tgggcacaga ttgaagaatc tgcccctgtt gaggtgggtg ggcctgactg ttgcccccca   1532
gggtcctaaa acttggatgg acttgtatag tgagagagga ggcctggacc gagatgtgag   1592
tcctgttgaa gacttcctct ctacccccca ccttggtccc tctcagatac ccagtggaat   1652
tccaacttga aggattgcat cctgctgggg ctgaacatgc ctgccaaaga cgtgtccgac   1712
ctacgttcct ggccccctcg ttcagagact gcccttctca cgggctctat gcctgcactg   1772
ggaaggaaac aaatgtgtat aaactgctgt caataaatga cacccagacc ttcc         1826

<210> SEQ ID NO 2
<211> LENGTH: 272
<212> TYPE: PRT
<213> ORGANISM: human

<400> SEQUENCE: 2

Met Ala Ala Lys Val Phe Glu Ser Ile Gly Lys Phe Gly Leu Ala Leu
1               5                   10                  15

Ala Val Ala Gly Gly Val Val Asn Ser Ala Leu Tyr Asn Val Asp Ala
            20                  25                  30

Gly His Arg Ala Val Ile Phe Asp Arg Phe Arg Gly Val Gln Asp Ile
        35                  40                  45

Val Val Gly Glu Gly Thr His Phe Leu Ile Pro Trp Val Gln Lys Pro
    50                  55                  60

Ile Ile Phe Asp Cys Arg Ser Arg Pro Arg Asn Val Pro Val Ile Thr
65                  70                  75                  80

Gly Ser Lys Asp Leu Gln Asn Val Asn Ile Thr Leu Arg Ile Leu Phe
                85                  90                  95

Arg Pro Val Ala Ser Gln Leu Pro Arg Ile Phe Thr Ser Ile Gly Glu
            100                 105                 110

Asp Tyr Asp Glu Arg Val Leu Pro Ser Ile Thr Thr Glu Ile Leu Lys
        115                 120                 125

Ser Val Val Ala Arg Phe Asp Ala Gly Glu Leu Ile Thr Gln Arg Glu
    130                 135                 140

Leu Val Ser Arg Gln Val Ser Asp Asp Leu Thr Glu Arg Ala Ala Thr
145                 150                 155                 160

Phe Gly Leu Ile Leu Asp Asp Val Ser Leu Thr His Leu Thr Phe Gly
                165                 170                 175
```

Lys Glu Phe Thr Glu Ala Val Glu Ala Lys Gln Val Ala Gln Gln Glu
            180                 185                 190

Ala Glu Arg Ala Arg Phe Val Val Glu Lys Ala Glu Gln Gln Lys Lys
        195                 200                 205

Ala Ala Ile Ile Ser Ala Glu Gly Asp Ser Lys Ala Ala Glu Leu Ile
    210                 215                 220

Ala Asn Ser Leu Ala Thr Ala Gly Asp Gly Leu Ile Glu Leu Arg Lys
225                 230                 235                 240

Leu Glu Ala Ala Glu Asp Ile Ala Tyr Gln Leu Ser Arg Ser Arg Asn
                245                 250                 255

Ile Thr Tyr Leu Pro Ala Gly Gln Ser Val Leu Leu Gln Leu Pro Gln
            260                 265                 270

<210> SEQ ID NO 3
<211> LENGTH: 21
<212> TYPE: RNA
<213> ORGANISM: Artificial Sequence
<220> FEATURE:
<223> OTHER INFORMATION: siRNA with homology to human gene

<400> SEQUENCE: 3
aaguucagcg uguccggcga g                                          21

<210> SEQ ID NO 4
<211> LENGTH: 21
<212> TYPE: RNA
<213> ORGANISM: Artificial Sequence
<220> FEATURE:
<223> OTHER INFORMATION: siRNA with homology to human gene

<400> SEQUENCE: 4
aacuuacgcu gaguacuucg a                                          21

<210> SEQ ID NO 5
<211> LENGTH: 21
<212> TYPE: DNA
<213> ORGANISM: Artificial Sequence
<220> FEATURE:
<223> OTHER INFORMATION: siRNA with homology to human gene
<220> FEATURE:
<221> NAME/KEY: misc_feature
<222> LOCATION: (20)..(21)
<223> OTHER INFORMATION: t at position 20 is dT
      t at position 21 is dT
<220> FEATURE:
<221> NAME/KEY: misc_feature
<222> LOCATION: (20)..(21)
<223> OTHER INFORMATION: t at position 20 is dT
      t at position 21 is dT

<400> SEQUENCE: 5
ugucaacauc acacugcgct t                                          21

<210> SEQ ID NO 6
<211> LENGTH: 21
<212> TYPE: DNA
<213> ORGANISM: Artificial Sequence
<220> FEATURE:
<223> OTHER INFORMATION: siRNA with homology to human gene
<220> FEATURE:
<221> NAME/KEY: misc_feature
<222> LOCATION: (20)..(21)
<223> OTHER INFORMATION: t at position 20 is dT
      t at position 21 is dT
<220> FEATURE:
<221> NAME/KEY: misc_feature
<222> LOCATION: (20)..(21)
<223> OTHER INFORMATION: t at position 20 is dT

```
      t at position 21 is dT

<400> SEQUENCE: 6
gcgcagugug auguugacat t                                              21

<210> SEQ ID NO 7
<211> LENGTH: 21
<212> TYPE: DNA
<213> ORGANISM: Artificial Sequence
<220> FEATURE:
<223> OTHER INFORMATION: siRNA with homology to human gene
<220> FEATURE:
<221> NAME/KEY: misc_feature
<222> LOCATION: (20)..(21)
<223> OTHER INFORMATION: t at position 20 is dT
      t at position 21 is dT
<220> FEATURE:
<221> NAME/KEY: misc_feature
<222> LOCATION: (20)..(21)
<223> OTHER INFORMATION: t at position 20 is dT
      t at position 21 is dT

<400> SEQUENCE: 7
agccagcttc ctcgcatctt t                                              21

<210> SEQ ID NO 8
<211> LENGTH: 21
<212> TYPE: DNA
<213> ORGANISM: Artificial Sequence
<220> FEATURE:
<223> OTHER INFORMATION: siRNA with homology to human gene
<220> FEATURE:
<221> NAME/KEY: misc_feature
<222> LOCATION: (20)..(21)
<223> OTHER INFORMATION: g at position 20 is dG
      g at position 21 is dG
<220> FEATURE:
<221> NAME/KEY: misc_feature
<222> LOCATION: (20)..(21)
<223> OTHER INFORMATION: g at position 20 is dG
      g at position 21 is dG

<400> SEQUENCE: 8
agatgcgagg aagctggctg g                                              21

<210> SEQ ID NO 9
<211> LENGTH: 21
<212> TYPE: DNA
<213> ORGANISM: Artificial Sequence
<220> FEATURE:
<223> OTHER INFORMATION: siRNA with homology to human gene
<220> FEATURE:
<221> NAME/KEY: misc_feature
<222> LOCATION: (20)..(21)
<223> OTHER INFORMATION: t at position 20 is dT
      t at position 21 is dT
<220> FEATURE:
<221> NAME/KEY: misc_feature
<222> LOCATION: (20)..(21)
<223> OTHER INFORMATION: t at position 20 is dT
      t at position 21 is dT

<400> SEQUENCE: 9
cccagaaauc acugugaaat t                                              21

<210> SEQ ID NO 10
<211> LENGTH: 21
<212> TYPE: DNA
<213> ORGANISM: Artificial Sequence
<220> FEATURE:
<223> OTHER INFORMATION: siRNA with homology to human gene
<220> FEATURE:
```

-continued

```
<221> NAME/KEY: misc_feature
<222> LOCATION: (20)..(21)
<223> OTHER INFORMATION: t at position 20 is dT
       t at position 21 is dT
<220> FEATURE:
<221> NAME/KEY: misc_feature
<222> LOCATION: (20)..(21)
<223> OTHER INFORMATION: t at position 20 is dT
       t at position 21 is dT

<400> SEQUENCE: 10
tttcacagug auuucugggt t                                        21

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer with homology to human
      gene

<400> SEQUENCE: 11
ctttgactgc cgttctcgac                                          20

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer with homology to human
      gene

<400> SEQUENCE: 12
tgggtggatt agttctccag c                                        21

<210> SEQ ID NO 13
<211> LENGTH: 23
<212> TYPE: DNA
<213> ORGANISM: Artificial Sequence
<220> FEATURE:
<223> OTHER INFORMATION: oligonucleotide primer with homology to human
      gene

<400> SEQUENCE: 13
ggtatcgtgg aaggactcat gac                                      23

<210> SEQ ID NO 14
<211> LENGTH: 23
<212> TYPE: DNA
<213> ORGANISM: Artificial Sequence
<220> FEATURE:
<223> OTHER INFORMATION: oligonucleotide primer with homology to human
      gene

<400> SEQUENCE: 14
atgccagtga gcttcccgtt cag                                      23
```